US011435367B2

(12) United States Patent
Yuan et al.

(10) Patent No.: US 11,435,367 B2
(45) Date of Patent: Sep. 6, 2022

(54) METHODS AND KITS FOR ASSAYING A VITAMIN D MOIETY

(71) Applicant: Diazyme Laboratories, Inc., San Diego, CA (US)

(72) Inventors: Chong-Sheng Yuan, San Diego, CA (US); Fakhri Ben Habib Saida, San Diego, CA (US)

(73) Assignee: Diazyme Laboratories, inc., San Diego, CA (US)

( * ) Notice: Subject to any disclaimer, the term of this patent is extended or adjusted under 35 U.S.C. 154(b) by 0 days.

(21) Appl. No.: 15/663,578

(22) Filed: Jul. 28, 2017

(65) Prior Publication Data

US 2018/0031581 A1 Feb. 1, 2018

Related U.S. Application Data

(60) Provisional application No. 62/368,940, filed on Jul. 29, 2016.

(51) Int. Cl.
*G01N 33/82* (2006.01)
*G01N 33/53* (2006.01)
*A61K 31/593* (2006.01)

(52) U.S. Cl.
CPC .......... *G01N 33/82* (2013.01); *A61K 31/593* (2013.01); *G01N 33/53* (2013.01)

(58) Field of Classification Search
CPC ...... A61K 31/593; G01N 33/53; G01N 33/82; G01N 33/54313; G01N 33/546; G01N 33/5304; G01N 33/54306; G01N 33/54333; G01N 21/82; G01N 2021/825; G01N 21/83; C07K 2317/32
See application file for complete search history.

(56) References Cited

U.S. PATENT DOCUMENTS

| | | | |
|---|---|---|---|
| 4,308,026 A * | 12/1981 | Mochida | G01N 33/54313 436/520 |
| 4,690,906 A | 9/1987 | Duheille et al. | |
| 4,703,018 A | 10/1987 | Craig et al. | |
| 5,223,441 A | 6/1993 | Ullman et al. | |
| 5,583,003 A * | 12/1996 | Hillyard | G01N 33/54306 435/7.25 |
| 5,821,020 A | 10/1998 | Hollis | |
| 6,375,949 B1 | 4/2002 | Hirano et al. | |
| 7,087,395 B1 | 8/2006 | Garrity | |
| 7,482,162 B2 | 1/2009 | Laurie et al. | |
| 7,964,363 B2 | 6/2011 | Armbruster et al. | |
| 8,133,694 B2 | 3/2012 | Armbruster et al. | |
| 2002/0106708 A1 | 8/2002 | Thomas et al. | |
| 2004/0091940 A1 | 5/2004 | Sawai | |
| 2004/0132104 A1 | 7/2004 | Sackrison et al. | |
| 2006/0246506 A1* | 11/2006 | Pulli | C07K 16/44 435/7.1 |
| 2009/0093445 A1 | 4/2009 | Kyriatsoulis et al. | |
| 2011/0033950 A1 | 2/2011 | Nilsen | |
| 2011/0097733 A1 | 4/2011 | Anciaux et al. | |
| 2011/0195438 A1 | 8/2011 | Kondou et al. | |
| 2014/0132104 A1 | 5/2014 | Tokizawa | |
| 2014/0162294 A1 | 6/2014 | Yuan et al. | |
| 2014/0273021 A1 | 9/2014 | Zielinski et al. | |
| 2014/0370616 A1* | 12/2014 | Gupta | G01N 33/82 436/501 |
| 2015/0212099 A1 | 7/2015 | Yuan | |
| 2015/0355202 A1 | 12/2015 | Uchida et al. | |
| 2016/0047825 A1 | 2/2016 | Poppe et al. | |
| 2017/0160273 A1 | 6/2017 | Nogami et al. | |

FOREIGN PATENT DOCUMENTS

| | | |
|---|---|---|
| CN | 101680890 A | 3/2010 |
| EP | 3491392 B1 | 3/2021 |
| JP | 8-211054 A | 8/1996 |
| JP | 9-318629 A | 12/1997 |
| JP | 2009-510415 A | 3/2009 |
| JP | 2009510415 A | 4/2009 |
| JP | 2016517004 A | 2/2016 |

(Continued)

OTHER PUBLICATIONS

Sadler, "Imprecision Profiling," Clin. Biochem. Rev., 2008, Suppl. 1, pp. S33-S36.*
Cox et al., "Immunoassay Methods," In: Assay Guidance Manual [Internet], published May 1, 2012; last update: Jul. 8, 2019.*
TechNote 304, "Light-Scattering Assays," 2013, pp. 1-7.*
H Yu, "Comparative studies of magnetic particle-based solid phase fluorogenic and electrochemiluminescent immunoassay," Journal of Immunological Methods, 218(1-2):1-8(1998).
Wang et al., "Rapid, Simple, and Sensitive Immunoagglutination Assay with SiO2 Particles and Quartz Crystal Microbalance for Quantifying Schistosoma japonicum Antibodies," Clinical Chemistry, 52(11 ):2065-2071 (2006).
International Search Report for international patent application PCT/US2017044504, dated Nov. 10, 2017, 4 pages.

(Continued)

*Primary Examiner* — Galina M. Yakovleva
(74) *Attorney, Agent, or Firm* — Rimon PC; Peng Chen

(57) ABSTRACT

The present invention provides methods and compositions, e.g., kits, for assaying a vitamin D moiety in a sample, comprising or using, inter alia, a buffer that is capable of dissociating a vitamin D moiety from its binding protein and/or a buffer of acidic pH, and at least two antibodies, e.g., at least two monoclonal antibodies, that are separately conjugated to particles, e.g., latex particles, wherein at least one of said antibodies (or the first antibody) has a specific binding affinity towards the vitamin D moiety, and at least another said antibody (or the second antibody) has a specific binding affinity towards the complex formed between the first antibody and the vitamin D moiety, if present in said sample. In some embodiments, the optical change due to the agglutination reaction between the antibodies and the vitamin D moiety is measured for determination of the amount of vitamin D content in the samples. Kits and reaction mixtures for assaying a vitamin D moiety in a sample are also provided.

14 Claims, 9 Drawing Sheets

(56) References Cited

FOREIGN PATENT DOCUMENTS

| | | |
|---|---|---|
| JP | 2016-517004 A | 6/2016 |
| WO | 02057797 A2 | 7/2002 |
| WO | 2002079782 A1 | 10/2002 |
| WO | 2002/079782 A1 | 7/2004 |
| WO | 2016/006398 A1 | 4/2009 |
| WO | 2010100487 A1 | 9/2010 |
| WO | 2012129650 A1 | 4/2012 |
| WO | 2012091569 A1 | 7/2012 |
| WO | 2012129650 A1 | 10/2012 |
| WO | 2011/010673 A1 | 1/2013 |
| WO | 2011010673 A1 | 1/2013 |
| WO | 2014122972 A1 | 8/2014 |
| WO | 2015116961 A1 | 8/2015 |
| WO | 2015200186 A1 | 12/2015 |
| WO | 2014/122972 A1 | 1/2017 |
| WO | 2014122972 A1 | 1/2017 |
| WO | 2016006398 A1 | 4/2017 |
| WO | 2018023066 A1 | 2/2018 |

OTHER PUBLICATIONS

Written Opinion for International Search Report for international patent application PCT/US2017044504, dated Nov. 10, 2017, 6 pages.
International Preliminary on Patentability for international patent application PCT/US2017044504, dated Jan. 29, 2019, 7 pages.
Communication pursuant to Rules 161(1) and 162 EPC for European patent application EP17755585.1, dated Mar. 7, 2019, 3 pages.
Fakhri B Sa Ida et al., "First 25-hydroxyvitamin D assay for general chemistry analyzers11," Expert Review of Molecular Diagnostics, vol. 15, No. 3, Mar. 1, 2015 (Mar. 1, 2015), pp. 313-323, XP055178192,ISSN: 1473-7159, DOI:10.1586/14737159.2015.988144.
Voluntary Amendment in response to Examiner's Report for Australian patent application AU2017301763, dated Jan. 16, 2019, 20 pages.
Responsive to the communication pursuant to Rules 161(1) and 162 EPC for European patent application EP17 755 585.1, dated Sep. 13, 2019, 15 pages.
Claims marked-up in response to the communication pursuant to Rules 161(1) and 162 EPC for European patent application EP17 755 585.1, dated Sep. 13, 2019, 7 pages.
Claims in response to the communication pursuant to Rules 161(1) and 162 EPC for European patent application EP17 755 585.1, dated Sep. 13, 2019, 4 pages.
Communication pursuant to Article 94(3) EPC for European patent application EP17 755 585.1, dated Feb. 12, 2020, 4 pages.
Notice of Reasons for Rejection for Japanese patent application 2019-504949, dated Mar. 6, 2020, 4 pages with extra 5 pages of English language equivalent or summary.
Amended Claims filed with the JPO on Sep. 4, 2020 for Japanese patent application 2019-504959, dated Sep. 4, 2020, 7 pages.
Amendment for Japanese patent application 2019-504959, dated Sep. 4, 2020, 9 pages.
Communication pursuant to Article 94(3) EPC for European patent application 17 755 585.1, dated Feb. 17, 2020, 5 pages.
Claims (mark-up) for European patent application 17 755 585.1, dated Aug. 18, 2020, 4 pages.
Claims (clear) for European patent application 17 755 585.1, dated Aug. 18, 2020, 4 pages.
Response to the communication pursuant to Article 94(3) EPC for European patent application 17 755 585.1, dated Aug. 18, 2020, 4 pages.
Official Action for Japanese patent application JP2019-504959, dated Feb. 2, 2021, 3 pages with extra 7 pages of English language equivalent or summary.
Communication under Rule 71(3) EPC for European patent application EP17755585.1, dated Oct. 16, 2020, 52 pageds.
Abstract of Japanese Laid-Open Publication No. 8-211054 in English for Japanese patent application JP08-211054A, dated Aug. 20, Aug. 20, 1996, 1 page.
Voluntary Amendment for Australian patent application AU2017301763, dated May 31, 2021, 10 pages.
1st Office Action for Chinese patent application CN2017800468348, dated Aug. 18, 2021, 14 pages with extra 15 pages of English language equivalent or summary.
Decision to Grant for European patent application EP17755585.1, dated Mar. 9, 2021, 2 pages.
Amended Claims for Japanese patent application JP2019-504959, dated May 6, 2021, 7 pages.
Amendment for Japanese patent application JP2019-504959, dated May 6, 2021, 4 pages.
Filing an Argument for Japanese patent application JP2019-504959, dated May 6, 2021, 12 pages.
Notice of Reasons for Rejection for Japanese patent application JP2019-504959, dated Oct. 28, 2021, 2 pages with extra 4 pages of English language equivalent or summary.
Danielli et al., "Rapid homogeneous detection of biological assays using magnetic modulation biosensing system," J Vis Exp. 2010;(40):1935. Published Jun. 13, 2010 doi:10.3791/1935.
Claims in response to the First Action for Chinese patent application CN201780046834.8, dated Mar. 2, 2022,4 pages with extra 6 pages of English language equivalent or summary.
Amended Claims filed with the JPO on Jan. 27, 2022 to response to the Penultimate Official Action for Japanese patent application JP2019-504959, dated Jan. 27, 2022, 7 pages.
Responsive to the communication pursuant to Rules 161(1) and 162 EPC for European patent application EP17755585.1, dated Sep. 13, 2019, 26 pages.
Communication of a notice of opposition for European patent application EP17755585.1, dated Jan. 12, 2022, 34 pages.
Communication of notices of opposition (R.79(1) EPC) for European patent application EP17755585.1, dated Jan. 18, 2022, 1 page.
Jay L. Bock, "The New Era of Automated Immunoassay," Am J Clin Pathol 2000;113:628-646.
Pulli et al., "One-Step Homogeneous Immunoassay for Small Analytes," Analytical Chemistry, vol. 77, No. 8, Apr. 15, 2005, 2637-2642.
U.S. Appl. No. 62/368,940, dated Jul. 29, 2016, 50 pages.
T68699 (Decision of Jan. 22, 2003 for European patent application EP91115262.7), dated Jan. 22, 2003, 13 pages.

* cited by examiner

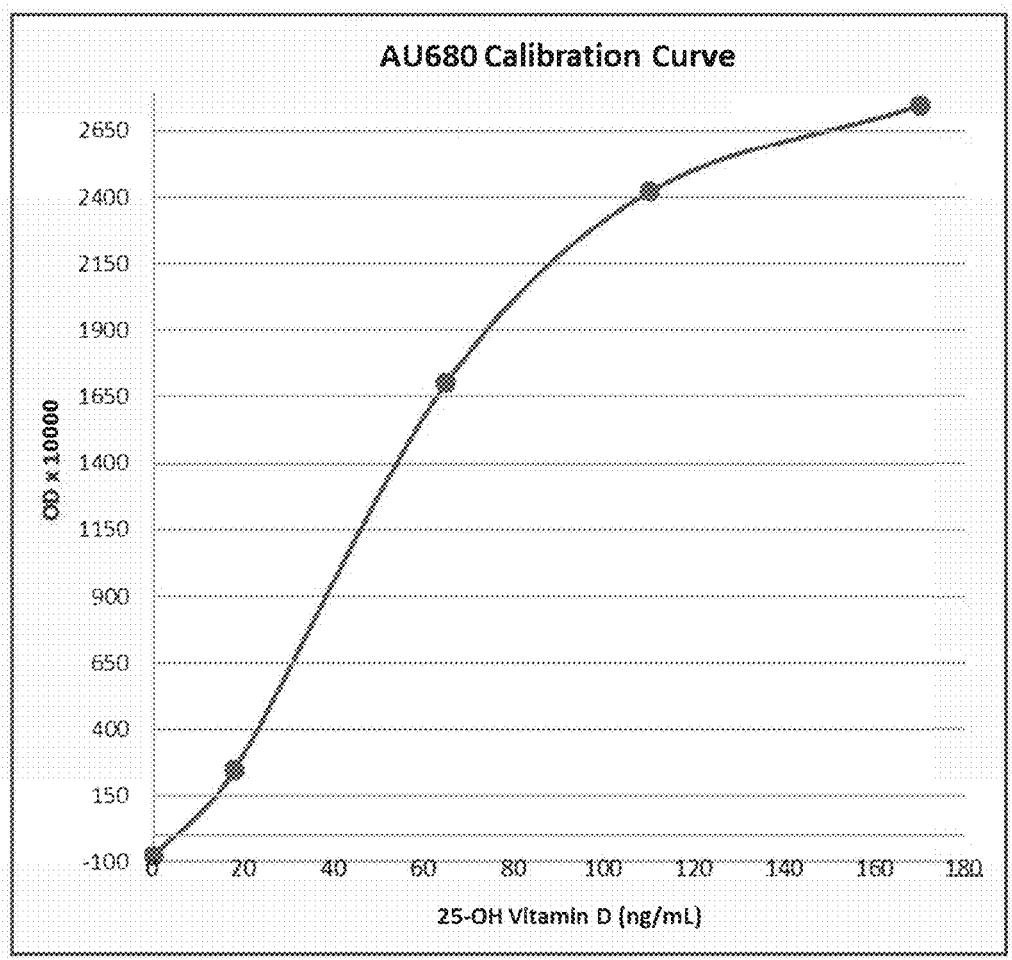
Figure 1. A typical calibration curve on AU680

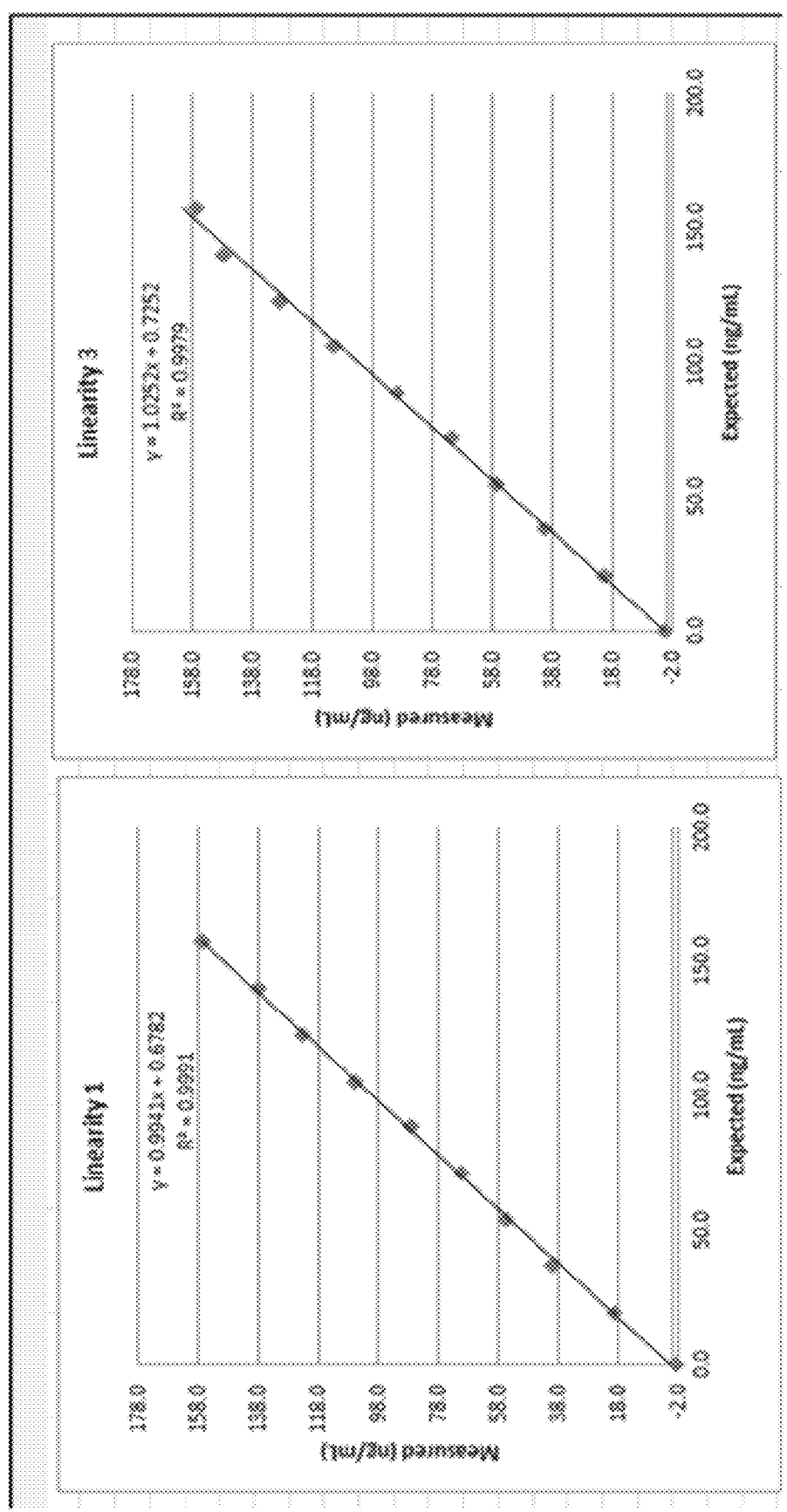
Figure 2. Assay linearity on AU 680 analyzer

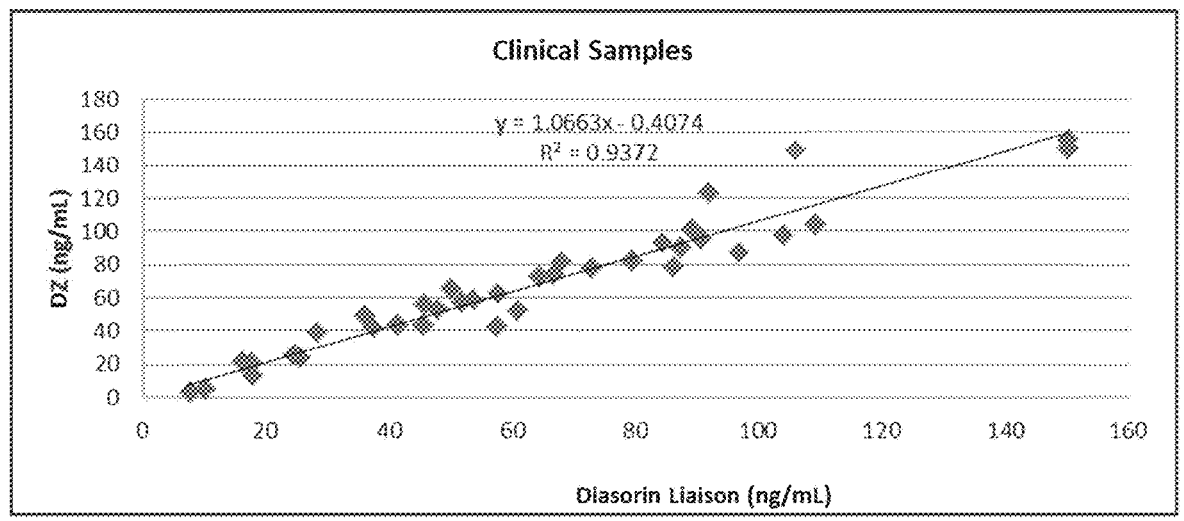
Figure 3. Assay accuracy in comparison with DiaSorin Liason method
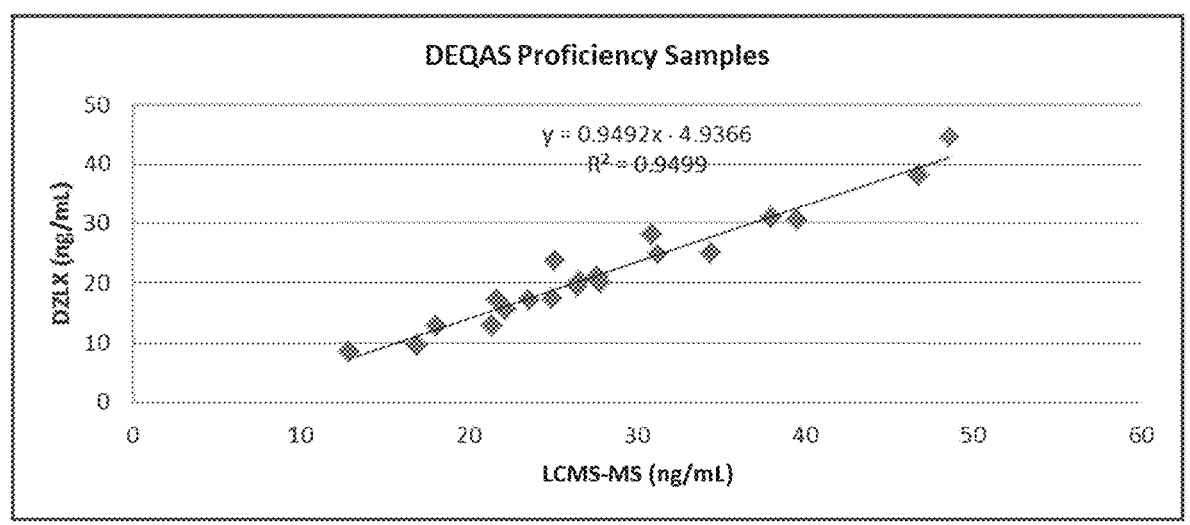
Figure 4. Assay accuracy in comparison with LC-MS/MS method

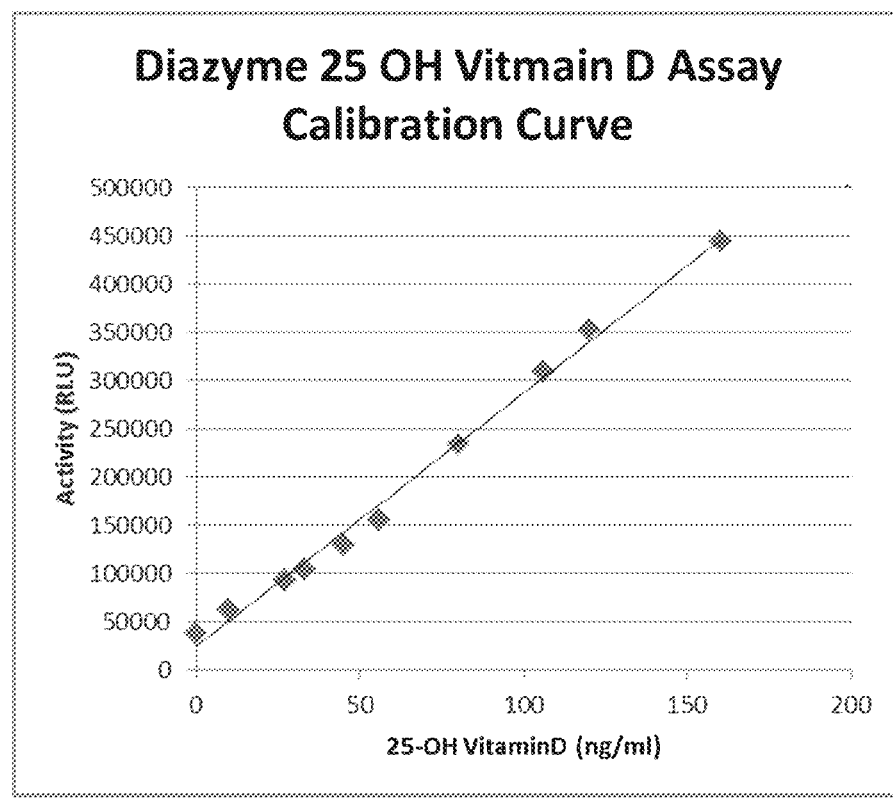
Figure 5. A typical calibration curve of chemiluminesent detection method

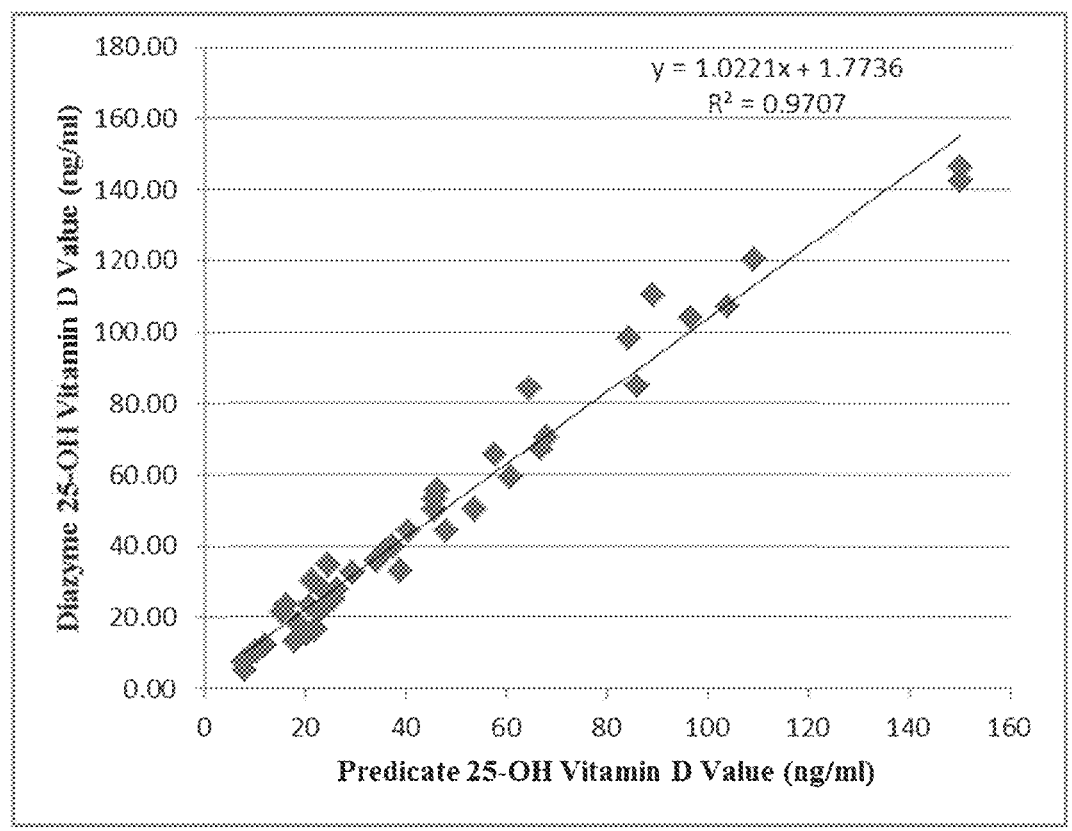
Figure 6. Method comparison data between the current invention method and a commercially available predicate method (immunoassay)

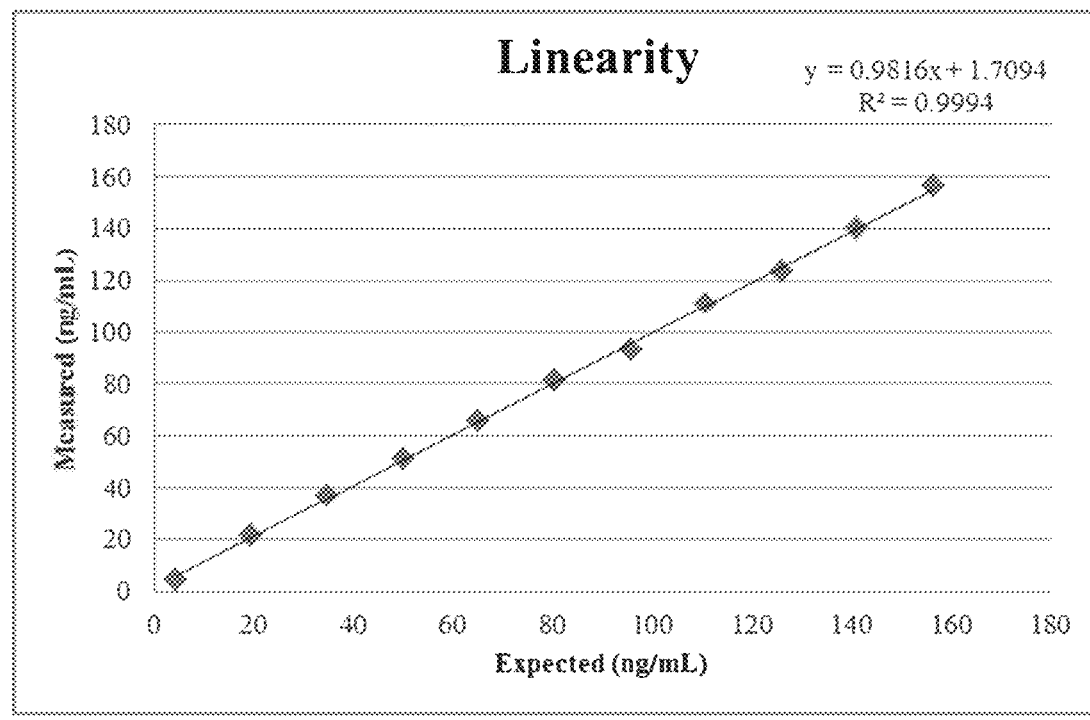
Figure 7. Linearity test results
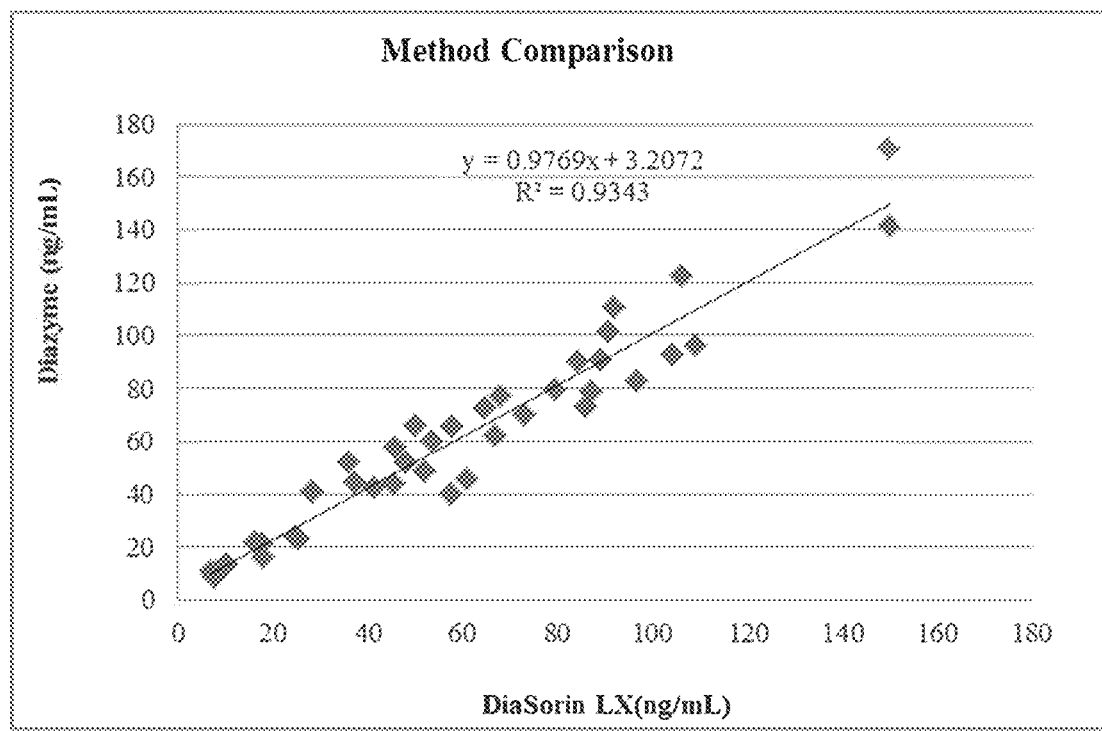
Figure 8. Method comparison results

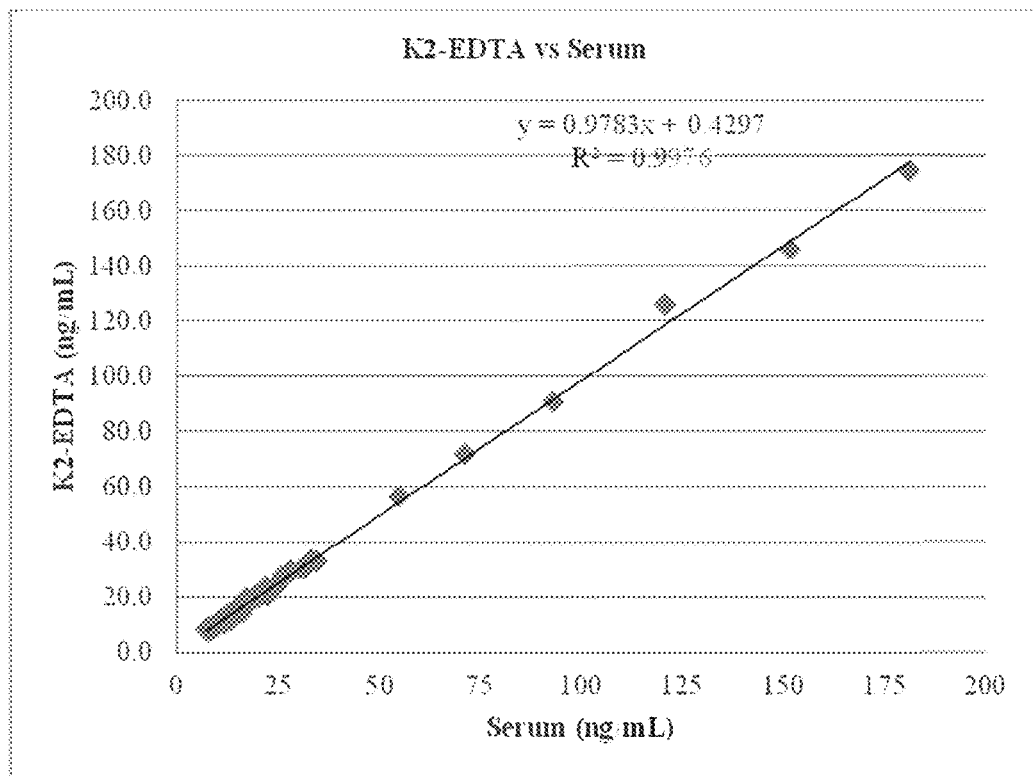
Figure 9. Matrix comparison results (K2-EDTA v. Serum)
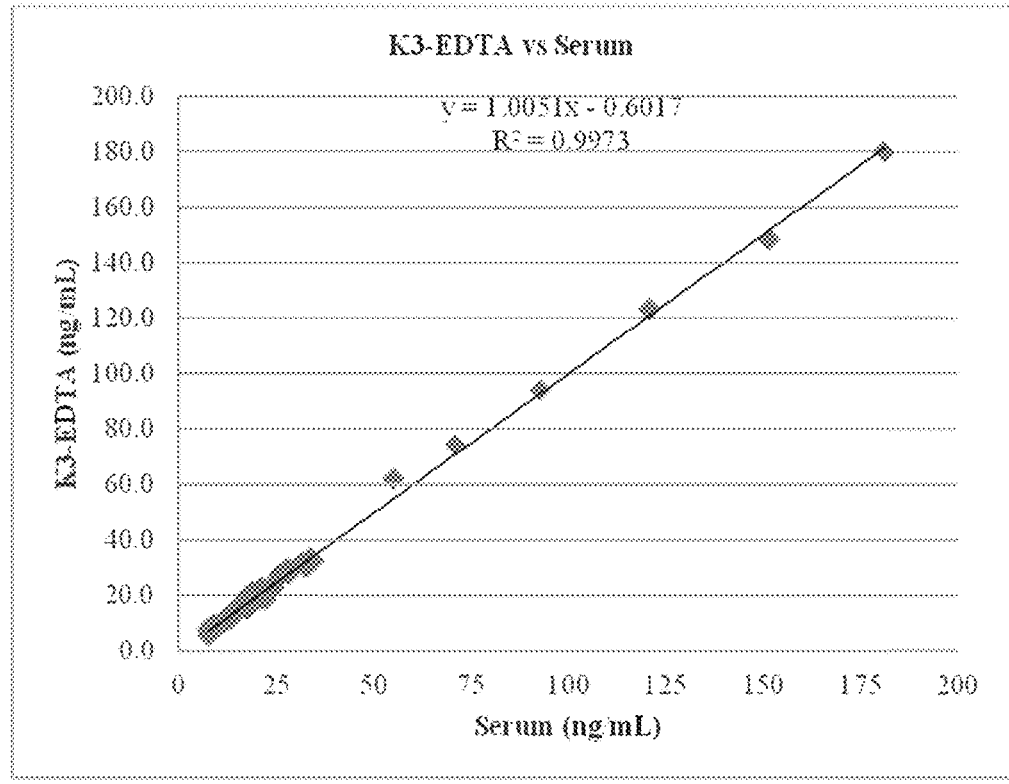
Figure 10. Matrix comparison results (K3-EDTA v. Serum)

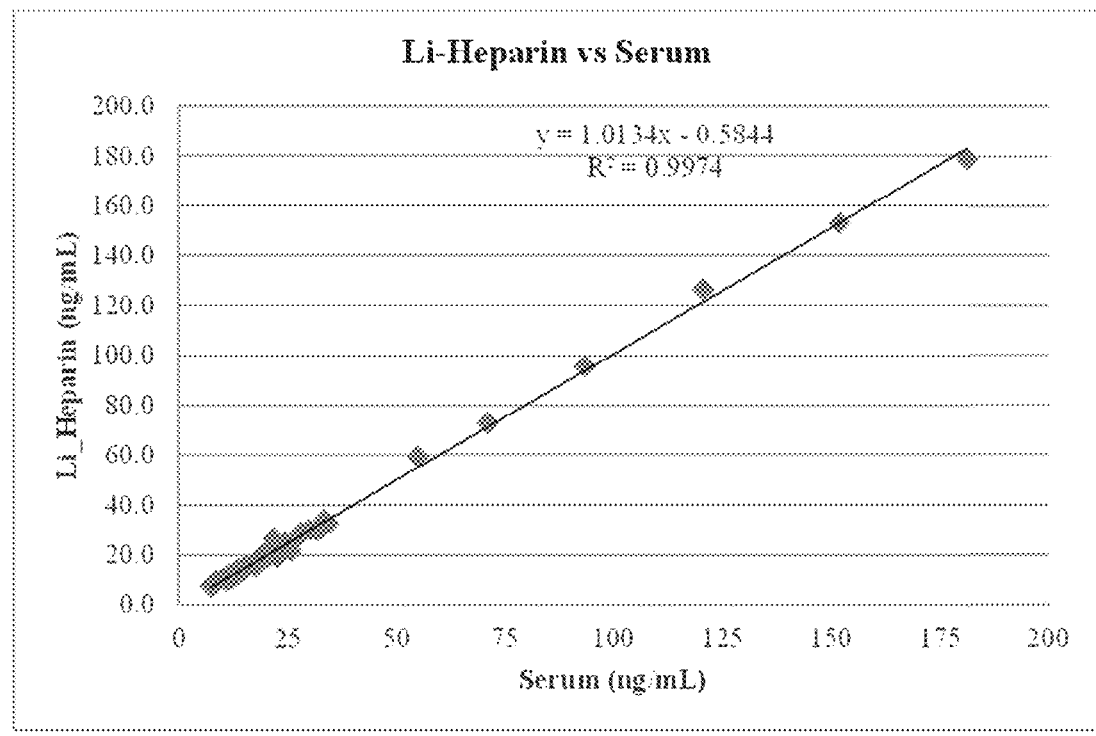
Figure 11. Matrix comparison results (K2-Li-Heparin v. Serum)
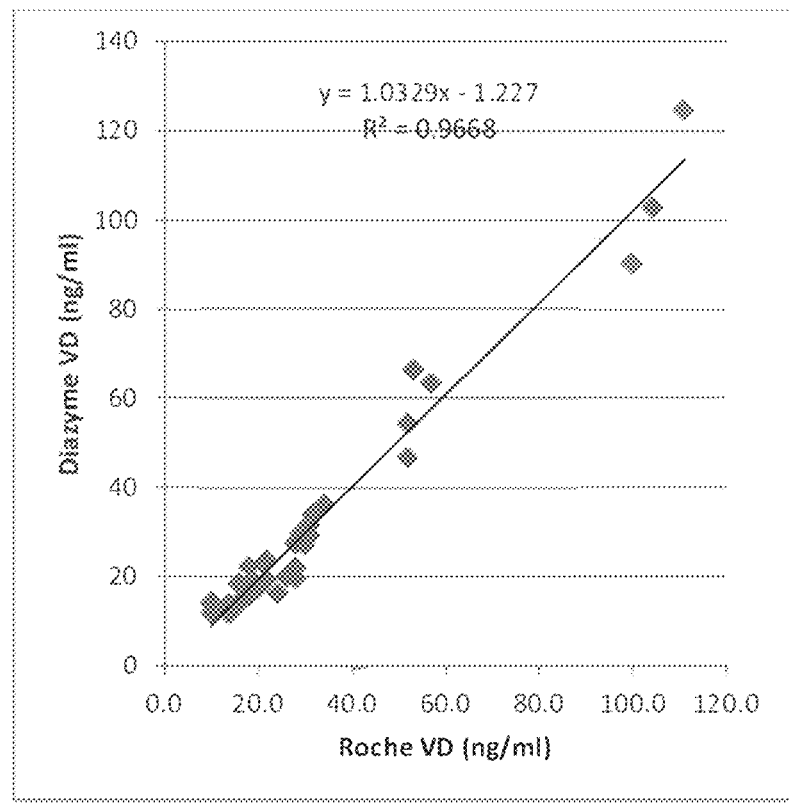
Figure 12. Method comparison results (v. Roche VD assay)

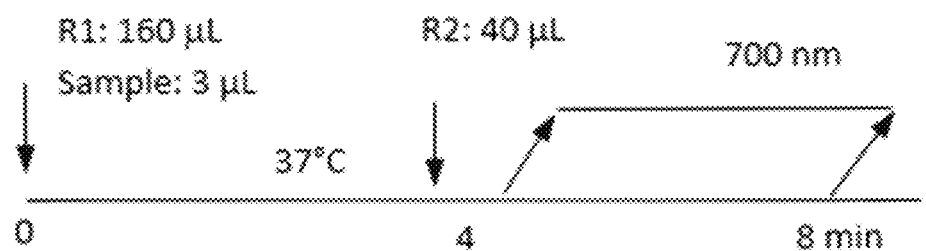
Figure 13. An Assay Procedure with Beckman AU 680 Analyzer

METHODS AND KITS FOR ASSAYING A VITAMIN D MOIETY

CROSS-REFERENCE TO RELATED APPLICATION

This application claims the priority benefit of U.S. provisional application Ser. No. 62/368,940, filed Jul. 29, 2016, the content of which is incorporated by reference in its entirety.

FIELD OF THE INVENTION

This invention generally relates to the field of vitamin D detection. In particular, the invention provides a novel methods and kits for assaying a vitamin D moiety in a sample such as a biological fluid.

BACKGROUND OF THE INVENTION

Vitamin D is a steroid-like, fat soluble prohormone. Vitamin D has two main forms: D2 (ergocalciferol) and D3 (cholecalciferol). Vitamin D3 can be manufactured by the body upon exposure to UV radiation. Both Vitamin D3 and Vitamin D2 are converted to the active hormone 1,25-dihydroxy Vitamin D through their metabolism in the liver and kidney.

Vitamin D3 is synthesized in skin by exposure to sunlight (ultraviolet radiation) and obtained from the diet primarily from fish liver oils and egg yolks. Vitamin D2 is obtained mainly from nutritional supplements and the only prescription drug in US for Vitamin D deficiency is made of Vitamin D2. Vitamin D3 or D2 is metabolized by the liver to 25(OH)D, which is then converted by the kidneys to 1,25 (OH)2D, 25(OH) Vitamin D is the major circulating form which reflects the levels of Vitamin D in the body, but 1,25(OH)2 Vitamin D is the most biologically active form.

Inadequate exposure to sunlight or low intake from diet or supplements may cause vitamin D deficiency. Vitamin D deficiency impairs bone mineralization, causing rickets in children and osteomalacia in adults and may contribute to osteoporosis. Recent studies have shown that Vitamin D deficiency is also linked to cancers, cardiovascular diseases, diabetes, multiple sclerosis, Parkinson disease, Alzheimer's disease, drug efficacy; and all-cause mortality.

A typical normal or sufficient range for Vitamin is about 30-100 ng/mL. Vitamin D level at about 10-30 ng/mL is considered deficient. Vitamin D level less than 10 ng/mL is considered severely deficient. Vitamin D level more than 150 ng/mL is considered toxic.

Various vitamin D assays are known in the art. For example, various vitamin D assays are disclosed in U.S. Pat. Nos. 5,821,020, 7,087,395 B1, 7,482,162 B2, 7,964,363 B2, 8,133,694 B2, U.S. patent publication No. 2004/0132104 A1 and WO 2012/091569 A1.

There remains a need for a reliable, sensitive and specific method for assaying a vitamin D moiety in a sample such as a biological fluid, particularly one that can be conducted as a homogeneous assay and/or is amenable to automated clinical chemistry analyzers in typical clinical laboratory settings.

BRIEF SUMMARY OF THE INVENTION

In one aspect, the present invention provides a method for assaying a vitamin D moiety in a sample, which method comprises: a) contacting a sample containing or suspected of containing a vitamin D moiety with a buffer that is capable of dissociating a vitamin D moiety from its binding protein and/or a buffer of acidic pH, and at least two antibodies, e.g., at least two monoclonal antibodies, that are attached to, e.g., separately attached to, surface(s) or particles, wherein one antibody, e.g., one monoclonal antibody or the first antibody, has a specific binding affinity towards the vitamin D moiety, and another antibody, e.g., another monoclonal antibody or the second antibody, has a specific binding affinity towards the complex formed between the first antibody and the vitamin D moiety; and b) assessing the binding between said specific antibodies and said vitamin D moiety to determine the presence, absence and/or amount of said vitamin D moiety in said sample. Optionally, the antibodies are different from a natural vitamin D binding protein for the vitamin D moiety.

In another aspect, the present invention provides a method for assaying a vitamin D moiety in a sample, which method comprises: a) contacting a sample containing or suspected of containing a vitamin D moiety with a buffer that is capable of dissociating a vitamin D moiety from its binding protein and/or a buffer of acidic pH, and at least two antibodies, e.g., at least two monoclonal antibodies, wherein at least one of said antibodies (or the first antibody) has a specific binding affinity towards the vitamin D moiety and is attached to a solid surface, e.g., solid surface of a microtiter plate or a particle, and at least another said antibody (or the second antibody) has a specific binding affinity towards the complex formed between said first antibody and said vitamin D moiety and is labelled with a signal generating moiety, and b) assessing binding between said antibodies, e.g., said specific antibodies, and said vitamin D moiety to determine the presence, absence and/or amount of said vitamin D moiety in said sample. Optionally, the antibodies are different from a natural vitamin D binding protein for the vitamin D moiety.

In still another aspect, the present invention provides a kit for assaying a vitamin D moiety in a sample, which kit comprise: a) a buffer that is capable of dissociating a vitamin D moiety from its binding protein and/or a buffer of acidic pH; b) at least two antibodies, e.g., at least two monoclonal antibodies, that are attached to, e.g., separately attached to, surfaces or particles such as latex particles, wherein one antibody, e.g., one monoclonal antibody or the first antibody has the affinity to bind with vitamin D moiety, and another antibody, e.g., another monoclonal antibody or the second antibody, has the affinity to bind with the complex formed between the first antibody and the vitamin D moiety.

In yet another aspect, the present invention provides a method for assaying a vitamin D moiety in a sample, which method comprises: a) contacting said sample with a first reagent comprising a buffer of acidic pH to dissociate said vitamin D moiety in said sample from its binding proteins; b) contacting said vitamin D moiety in said sample from step a) with a second reagent comprising particles, e.g., magnetic particles, coated with a first antibody that has a specific binding affinity to said vitamin D moiety to form a vitamin D moiety/first antibody complex; and c) contacting said vitamin D moiety/first antibody complex with a third reagent comprising a second antibody labelled with a signal generating molecule to form a complex among said vitamin D moiety, said first antibody complex and said second antibody labelled with a signal generating moiety or molecule; and d) assessing said signal from said complex among said vitamin D moiety, said first antibody and said second antibody to determine the presence, absence and/or amount of the vitamin D moiety in said sample. In some embodiments, the signal generating moiety or molecule is selected from the group consisting of acridinium ester, isoluminol, alkaline phosphatase, horse radish peroxidase and fluoresin.

In yet another aspect, the present invention provides a reaction mixture for assaying a vitamin D moiety in a sample, which reaction mixture comprises: a buffer that is capable of dissociating a vitamin D moiety from its binding protein and/or a buffer of acidic pH; and at least two antibodies, e.g., at least two monoclonal antibodies, that are attached to, e.g., separately attached to, surface(s) or particles such as latex particles, wherein one antibody, e.g., one monoclonal antibody or the first antibody has the affinity to bind with vitamin D moiety, and another antibody, e.g., another monoclonal antibody or the second antibody, has the affinity to bind with the complex formed between the first antibody and the vitamin D moiety.

In some embodiments, the first antibody can be coated on surface(s) or particles such as magnetic particles, and another antibody or the second antibody can be labelled with signal generating molecules such as enzymes (e.g., alkaline phosphatase and peroxidase), or a chemiluminescent signal generating molecule such as acridinium ester, isoluminol, or a fluorescent molecule such as fluorescein and green fluorescent protein. In the presence of a vitamin D moiety in the reaction mixture, the second antibody binds to the complex formed between the vitamin D moiety from a sample and the first antibody coated on the surface(s) or particles to form a complex, e.g., a "sandwich" complex (first antibody-vitamin D-second antibody), and the amount of the "sandwich" formed on the surface(s) or particles is proportional to the amount of the vitamin D moiety in the sample, and can be quantitatively assessed by detecting the signal from the signal generating molecule that is labelled on the second antibody molecules.

In some embodiments, the at least two antibodies can be attached to a same particle or surface, or same type of particle(s) or surfaces. In other embodiments, the at least two antibodies can be attached to different particles or surfaces, or different types of particles or surfaces.

In some embodiments, the present methods and kits can use or incorporate selected elements or features of the methods and kits described and/or claimed in U.S. patent application Ser. Nos. 13/707,514 and 14/169,118, and PCT Application No. PCT/US2015/013831, which applications are incorporated by reference in their entireties.

BRIEF DESCRIPTION OF THE DRAWINGS

FIG. 1 illustrates an exemplary or a typical calibration curve of total 25(OH)D assay using the latex enhanced immunoassay method on an AU680 analyzer.

FIG. 2 illustrates an exemplary or a typical linearity curve of total 25(OH)D assay using latex particle enhanced immunoassay method on an AU680 analyzer.

FIG. 3 illustrates an exemplary or a typical method comparison data of total 25(OH)D assay using latex enhanced immunoassay method in comparison with a commercially available chemiluminescent immunoassay method (DiaSorin assay).

FIG. 4 illustrates an exemplary or a typical method comparison data of total 25(OH)D assay using latex particle enhanced immunoassay method in comparison with a gold standard method, the LC-MS/MS method.

FIG. 5 illustrates an exemplary or a typical calibration curve of total 25(OH)D assay using magnetic particle based immunoassay detection method.

FIG. 6 illustrates an exemplary or a typical method comparison data of total 25(OH)D assay using magnetic particle based immunoassay detection method in comparison with a commercially available chemiluminescent immunoassay method.

FIG. 7 illustrates exemplary linearity test results.

FIG. 8 illustrates exemplary method comparison results.

FIG. 9 illustrates exemplary matrix comparison results (K2-EDTA v. Serum).

FIG. 10 illustrates exemplary matrix comparison results (K3-EDTA v. Serum).

FIG. 11 illustrates exemplary matrix comparison results (K2-Li-Heparin v. Serum).

FIG. 12 illustrates exemplary method comparison results (v. Roche VD assay).

FIG. 13 illustrates the assay procedure with BECKMAN AU 680 analyzer.

DETAILED DESCRIPTION OF THE INVENTION

For clarity of disclosure, and not by way of limitation, the detailed description of the invention is divided into the subsections that follow.

A. Definitions

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "vitamin D moiety" refers to all members or forms of the Vitamin D family which is a group of fat-soluble secosteroids responsible for intestinal absorption of calcium and phosphate. Exemplary vitamin D forms include vitamin $D_1$, $D_2$ (ergocalciferol), $D_3$ (cholecalciferol), $D_4$, and $D_5$. Exemplary vitamin D moieties also include calcidiol, which is also known as calcifediol (INN), 25-hydroxycholecalciferol, or 25-hydroxyvitamin D—abbreviated 25(OH)D; and which is the specific vitamin D metabolite that is measured in serum to determine a person's vitamin D status, and calcitriol, the biologically active form of vitamin D. In some embodiments, "vitamin D moiety" refers to 25-hydroxyvitamin D—abbreviated as 25(OH)D including D2 and D3 forms.

As used herein, "antibody" includes not only intact polyclonal or monoclonal antibodies, but also fragments thereof (such as Fab, Fab', F(ab')2, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class. As used herein, the term "specifically binds" refers to the specificity of a binding reagent, e.g., an antibody, such that it preferentially binds to a defined analyte or target e.g., a vitamin D moiety. Recognition by a binding reagent or an antibody of a particular analyte or target in the presence of other potential targets is one characteristic of such binding. In some embodiments, a binding reagent that specifically binds to an analyte avoids binding to other interfering moiety or moieties in the sample to be tested.

A "vitamin D binding protein" is also known as gc-globulin (group-specific component). In some embodiments, a "vitamin D binding protein" refers to a Vitamin D-binding protein in the albumin family. A "vitamin D binding protein" is often found in plasma, ascitic fluid, cerebrospinal fluid and/or on the surface of many cell types. A "vitamin D binding protein" often binds to vitamin D and its metabolites and transports them to target tissues in vivo. An exemplary "vitamin D binding protein" in humans is encoded by the GC gene. In some embodiments, a "vitamin D binding protein" refers to a Vitamin D-binding protein known in the art, e.g., a vitamin D binding protein as described in the website: https://en.wikipedia.org/wiki/Albumin.

In some embodiments, "ascetic fluid" is used as described in the website: https://en.wikipedia.org/wiki/Ascites. In some embodiments, "cerebrospinal fluid" is used as described in the website: https://en.wikipedia.org/wiki/Cerebrospinal fluid.

As used herein the term "assessing" is intended to include quantitative and qualitative determination in the sense of obtaining an absolute value for the amount or concentration of the analyte present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further sub stance.

As used herein the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "blood sample" refers to a whole blood sample or a plasma or serum fraction derived therefrom. Preferably, the blood sample refers to a human blood sample such as whole blood or a plasma or serum fraction derived therefrom. Also preferably, the blood sample is pre-treated before the assay by removing substantially all hemoglobin (i.e., red blood cells) in order to eliminate or significantly reduce the oxidative interference from the hemoglobin molecules.

As used herein the term "whole blood" refers to a blood sample that has not been fractionated and contains both cellular and fluid components. As used herein, "whole blood" refers to freshly drawn blood which is tested before it clots, or a conventionally-drawn blood sample, which may be drawn into a vacutainer, and which may contain an anticoagulant, such as lithium-heparin, EDTA etc., or to which one or more other standard clinical agents may be added in the course of routine clinical testing.

As used herein, the phrase "substantially all hemoglobin has been removed" refers to a blood sample wherein preferably at least about 50%, 60% or 70%, more preferably, at least about 80%, 90% or 95%, and most preferably, at least about 96%, 97%, 98%, 99 or 100% of all hemoglobin-containing red blood cells in the sample have been removed to eliminate or significantly reduce the oxidative interference from hemoglobin.

As used herein, the term "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as whole human serum. Further, as used herein, "serum" refers to blood plasma from which clotting factors (e.g., fibrinogen) have been removed.

As used herein, the term "fluid" refers to any composition that can flow. Fluids thus encompass compositions that are in the form of semi-solids, pastes, solutions, aqueous mixtures, gels, lotions, creams and other such compositions.

As used herein, the term "disease" or "disorder" refers to a pathological condition in an organism resulting from, e.g., infection or genetic defect, and characterized by identifiable symptoms.

As used herein, "contacting" means bringing two or more components together. "Contacting" can be achieved by mixing all the components in a fluid or semi-fluid mixture. "Contacting" can also be achieved when one or more components are brought into contact with one or more other components on a solid surface such as a solid tissue section or a substrate.

As used herein, the term "comparing" generally means examining in order to note similarities or differences between two or more values. Preferably, "comparing" refers to quantitative comparisons such as, for example, subtracting one value from another, calculating a ratio of two values, calculating a percentage of one value with respect to another, or combining these types of calculations to produce a single number. As used herein, "comparing" further refers to comparisons made by a human, comparisons made by a computer or other processor, and comparisons made by a human in combination with a computer or other processor.

It is understood that aspects and embodiments of the invention described herein include "consisting" and/or "consisting essentially of" aspects and embodiments.

Other objects, advantages and features of the present invention will become apparent from the following specification taken in conjunction with the accompanying drawings.

B. Methods for Assaying a Vitamin D Moiety

In one aspect, the present invention provides a method for assaying a vitamin D moiety in a sample, which methods comprises: a) contacting a sample containing or suspected of containing a vitamin D moiety with a buffer of acidic pH, at least two antibodies, e.g., at least two monoclonal antibodies, that are attached to, e.g., separately attached to, particles or surface(s), e.g., latex particles, one of the antibodies or the first antibody having a specific binding affinity towards said vitamin D moiety, and the another antibody or the second antibody having a specific binding affinity towards the complex formed between the first antibody and the said vitamin D moiety; and b) assessing binding (e.g., the degree of agglutination of particles due to formation of a complex formed among or between said at least two antibodies and said vitamin D moiety, e.g., a sandwich complex between said two monoclonal antibodies and said vitamin D moiety to determine the presence, absence and/or amount of said vitamin D moiety in said sample. Optionally, the antibodies are different from a natural vitamin D binding protein for the vitamin D moiety. In some embodiments, the at least two antibodies can be attached to a same particle or surface, or same type of particle(s) or surfaces. In other embodiments, the at least two antibodies can be attached to different particles or surfaces, or different types of particles or surfaces.

In another aspect, the present invention provides a method for assaying a vitamin D moiety in a sample, which method comprises: a) contacting a sample containing or suspected of containing a vitamin D moiety with a buffer that is capable of dissociating a vitamin D moiety from its binding protein and/or a buffer of acidic pH, and at least two antibodies, e.g., at least two monoclonal antibodies, wherein at least one of said antibodies (or the first antibody) has a specific binding affinity towards the vitamin D moiety and is attached to a solid surface, e.g., solid surface of a microtiter plate or a particle, and at least another said antibody (or the second antibody) has a specific binding affinity towards the complex formed between said first antibody and said vitamin D moiety and is labelled with a signal generating moiety, and b) assessing binding between said antibodies, e.g., said specific antibodies, and said vitamin D moiety to determine the presence, absence and/or amount of said vitamin D moiety in said sample. Optionally, the antibodies are different from a natural vitamin D binding protein for the vitamin D moiety.

In some embodiments, the present methods do not comprise a step of removing protein from the sample (See e.g., U.S. Pat. No. 5,821,020), such as the natural vitamin D binding protein for the vitamin D moiety, prior to assessing binding between the specific antibodies and the vitamin D moiety. In other embodiments, the present methods do not comprise any wash step.

The present methods can be conducted in any suitable assay format. In some embodiments, the present methods are conducted as a homogeneous assay. In other embodiments, the present methods are conducted as a heterogeneous assay.

A sample can be contacted with a buffer of acidic pH and two antibodies, e.g., two monoclonal antibodies, that are separately coated on particles, e.g., latex particles, in a single step, or in multiple steps, e.g., 2 or 3 steps. The exemplary multiple step contact order can be: 1) a buffer of acidic pH, incubating for a period of time before addition of the latex particles that are separately coated with the two said monoclonal antibodies; 2) a buffer of acidic pH, latex particles that coated with the first antibody, incubating for a period of time before addition of the latex particles coated with the said second antibody.

The pH in a final reaction mixture comprising the sample, the acid pH buffer, the particles, e.g., latex particles, separately coated with the two specific antibodies can be at any suitable value or range. In some embodiments, the pH in a final reaction mixture comprising the sample, the acidic pH buffer and the latex particles is at 2.5 or higher. In other embodiments, the pH in a final reaction mixture comprising the sample, the acidic pH buffer and the latex particles is at 13 or lower. In still other embodiments, the pH in a final reaction mixture comprising the sample, the acidic pH buffer and the latex particles is in a range from about 2.5 to about 13, e.g., at about 2.5, 3, 3.5. 4, 4.5, 5, 5.5, 5.6, 5.7, 5.8, 5.9, 6, 6.5, 7, 7.5, 8, 8.5, 9, 9.5, 10, 10.5, 11, 11.5, 12, 12.5, or 13.

In some embodiments, the present methods do not comprise a step of contacting the sample with a vitamin D releasing composition comprising a cyclodextrin, a sodium salicylate and NaOH, such as the vitamin D releasing composition disclosed in U.S. Pat. No. 7,087,395 B1.

In some embodiments, the present methods do not comprise a step of contacting the sample with a perfluoro alkyl acid, or a salt thereof, to release 25(OH) vitamin D from vitamin D binding protein, such as the step disclosed in WO 2012/091569 A1.

In some embodiments, the present methods do not comprise a step of contacting the sample with a serine protease with endo- and exoproteolytic activity to digest vitamin D binding proteins in the sample, such as the step disclosed in U.S. Pat. No. 7,964,363 B2.

The present methods can be used for any suitable purpose. In some embodiments, the present methods can be used to assess status of the vitamin D moiety in a subject, and the sample is a biological sample obtained and/or derived from the subject. The present methods can be used for assess status of the vitamin D moiety in any suitable subject, e.g., a mammal, a non-human mammal, a human or an experimental animal.

The present methods can be used for assaying a vitamin D moiety in any suitable sample. In some embodiments, the sample is a biological fluid, e.g., whole blood, plasma, serum or urine.

The present methods can be used for assaying any suitable vitamin D moiety in a sample. In some embodiments, the vitamin D moiety is vitamin $D_3$, vitamin $D_2$, a vitamin D metabolite or 1,25-dihydroxyvitamin $D_3$ [1,25(OH)$_2$D$_3$]. In other embodiments, the vitamin D moiety is 25-hydroxyvitamin D (25(OH)D), e.g., 25(OH)D3, 25(OH)D2 or a sum of 25(OH)D2 and 25(OH)D3.

Any acidic pH buffer can be used in the present methods. In some embodiments, the acidic pH buffer can be sodium acetate, sodium citrate, or phosphoric acid, or other buffers that have buffer functions in the acidic pH rage.

In other embodiments, the antibody specifically binds to 25(OH)D and the antibody specifically binds to the complex of 25(OH)D and the first antibody can be in any suitable forms. For example, a polyclonal antibody or a monoclonal antibody or fragments of the antibodies such as Fab fragment or a single chain antibody, can be used. In still other embodiments, exemplary antibodies disclosed in U.S. patent publication No. 2011/0097733 A1 can be used.

Any suitable particle can be used in the present particle based assay formats. In some embodiments, the particle comprises polystyrene, polymethyl methacrylate, polymethyl naphthalene, poly(divinylbenzene), polyvinyl naphthalene, co-polymer of styrene, acrylic acid divinylbenzene, naphathalene, carbon 60, magnetic beads, gold, silver, silica, silicon dioxide, chromium dioxide, and/or titanium dioxide. In other embodiments, the particle is a nanoparticle. The nanoparticle can have any suitable size or diameter. For example, the nanoparticle can have any diameter ranging from about 30 nm to about 500 nm, e.g., about 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, or 500 nm.

The present methods can be used in any suitable assay format. In some embodiments, the present methods are conducted using a particle-enhanced immunoturbidimetric method. See e.g., U.S. Pat. No. 4,703,018. In other embodiments, the present methods are conducted using a particle-enhanced immunonephelometric method. See e.g., U.S. Pat. No. 4,690,906. In still other embodiments, the present methods are conducted using a magnetic particle (bead) based immunoassay method. See e.g., Yu et al., Journal of Immunological Methods, 218(1-2):1-8 (1998). In yet other embodiments, the present methods are conducted using a particle based immunoagglutination assay method. See e.g., Wang et al., Clinical Chemistry, 52(11):2065-2071 (2006).

In some embodiments, the size of magnetic particles can be ranged from 500 to 2000 nanometers, preferably from 800-1500 nanometers.

In some embodiments, the magnetic particles are conjugated with the first antibody, and the second antibody is conjugated with signaling molecules such as acridinium ester, isoluminol, alkaline phosphatase, or horse radish peroxidase.

In some embodiments, the vitamin D assay is performed using a two-step chemiluminescent immunoassay format. Samples are contacted with the acidic pH buffer, and followed by an incubation period of time before addition of an antibody conjugated on particles, e.g., magnetic particles. After incubation, the particles, e.g., magnetic particles, are washed 1-3 times with a washing buffer, and re-suspended in a buffer before addition of a second antibody labelled with a signaling molecule. After incubation, the magnetic particles are washed again, and re-suspended in a buffer before addition of a substrate needed for chemiluminescent reaction.

In some embodiments, the vitamin D assay is performed using a one-step chemiluminescent immunoassay format. Samples are contacted with the acidic pH buffer, the particles, e.g., magnetic particles, coated with the first antibody and the second antibody labelled with a signaling molecule at the same time. After an incubation period of time, the particles, e.g., magnetic particles, are washed 1-3 times and re-suspended in a buffer before addition of a substrate needed for the chemiluminescent reaction.

In some embodiments, the present methods are conducted using a homogeneous assay format. In other embodiments, the present methods are conducted using a heterogeneous assay format. In still other embodiments, the present methods are conducted using a sandwich or competitive assay format. In yet other embodiments, the present methods are conducted using a format of an enzyme-linked immunosorbent assay (ELISA).

Any suitable homogenous assay format can be used. In some embodiments, a homogenous assay is conducted in a single reaction mixture without phase separation or washing step, such as the particle separation and washing steps disclosed in U.S. patent publication No. U.S. 2004/0132104 A1 or U.S. Pat. No. 8,133,694 B2.

The present methods can be conducted with any suitable reaction time. In some embodiments, the present methods have a total assay time that is at about 60 minutes or shorter, e.g., about 59, 58, 57, 56, 55, 54, 53, 52, 51, 50, 49, 48, 47, 46. 45., 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute. For example, the present methods can have an assay time from initiation, e.g., addition of a sample and/or a reagent(s), to signal readout time, that is at about 60 minutes or shorter, e.g., about 59, 58, 57, 56, 55, 54, 53, 52, 51, 50, 49, 48, 47, 46. 45., 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute.

The present methods can be conducted on any suitable analytic instruments. In some embodiments, the present methods are conducted on a general chemistry analyzer or a clinical chemistry analyzer, e.g., general chemistry analyzer or clinical chemistry analyzer from ROCHE, HITACHI, MODULAR P, COBAS series, BECKMAN/OLYMPUS AU series, BECKMAN SYNCHRON and DXC series, or ABBOT ARCHITECT series.

The present methods can be conducted to achieve any suitable precision. In some embodiments, the present methods can be conducted to achieve a precision or CV of about 30% or less, e.g., about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. For example, the present methods can be conducted to achieve a precision or CV of about 5% or less, e.g., about 5%, 4%, 3%, 2.5%, 2%, 1.5% 1%, 0.5% or less for a vitamin D moiety level of about 30 ng/ml or less, e.g., about 30 ng/ml, 25 ng/ml, 20 ng/ml, 15 ng/ml, 10 ng/ml, 5 ng/ml, 4 ng/ml, 3 ng/ml, 2 ng/ml, 1 ng/ml, or less. In another example, the present methods can be conducted to achieve a precision or CV of about 10% or less, e.g., about 10%, 9%, 8%, 7%, 6%, 5%, 4.5%, 4.0%, 3%, 2.5%, 2%, 1.5% 1%, 0.5% or less for a vitamin D moiety level of about 100 ng/ml or less, e.g., about 100 ng/ml, 90 ng/ml, 80 ng/ml, 70 ng/ml, 60 ng/ml, 50 ng/ml, 40 ng/ml, 30 ng/ml, 20 ng/ml, 10 ng/ml, or less.

C. Kits for Assaying a Vitamin D Moiety and Uses Thereof

In another aspect, the present invention provides a kit for assaying a vitamin D moiety in a sample, which kit comprises: a) a buffer that is capable of dissociating a vitamin D moiety from its binding protein and/or a buffer of acidic pH (R1); b) surface(s) or particles, e.g., latex particles, (R2) coated, e.g., separately coated, with at least two antibodies, one of the antibodies or the first antibody having a specific binding affinity towards vitamin D moiety, and another antibody or the second antibody having a specific binding affinity towards the complex formed between the first antibody and the vitamin D moiety. Optionally, the antibodies are different from a natural vitamin D binding protein for the vitamin D moiety. In some embodiments, the at least two antibodies can be attached to a same particle or same type of particle(s) or surface(s). In other embodiments, the at least two antibodies can be attached to different particles or surfaces, or different types of particles or surfaces.

Any suitable buffer of acidic pH can be used in the present kits. In some embodiments, the acidic pH buffer is the sodium acetate buffer, or sodium citrate buffer or phosphoric acid buffer.

Any suitable antibody combination comprising one antibody or the first antibody specifically binds to vitamin D moiety and the other antibody or the second antibody specifically binds to the complex formed between the first antibody and the vitamin D moiety can be used. Antibodies in any suitable forms can be used. For example, a polyclonal antibody or a monoclonal antibody, fragment of an antibody such as Fab fragment, or single chain antibody can be used. In still other embodiments, exemplary antibodies disclosed in U.S. patent publication No. 2011/0097733 A1 can be used.

The present kits can comprise any additional suitable reagents or components. In some embodiments, the present kits further comprise means for assessing binding between the specific antibodies and the vitamin D moiety to determine the presence, absence and/or amount of the vitamin D moiety in the sample.

The reagents or components in the present kits can be formulated or arranged in any suitable fashion or form. In some embodiments, the present kits comprise the following reagents: (1) a first assay reagent (R1) comprising a buffer of acidic pH; (2) a second assay reagent (R2) comprising two specific antibodies that are coated, e.g., separately coated, on surface(s) or particles, e.g., latex particles, one antibody or the first antibody having an affinity against the vitamin D moiety, and the other antibody or the second antibody having an affinity against the complex formed between the first antibody and vitamin D moiety.

The above kits can be used in a method for assaying a vitamin D moiety in a sample, which method comprises: a) forming a mixture of a sample and the first assay reagent and incubating the mixture for a period of time before adding the second assay reagent (e.g., latex particles coated with specific antibodies) to the mixture; and b) quantifying the amount of a vitamin D moiety, e.g., 25(OH)D, in the sample by measuring the optical change of the reaction mixture and using a set of vitamin D moieties, e.g., a set of 25(OH)D calibrators.

In still other embodiments, the present kits comprise (1) a first assay reagent comprising a buffer of acidic pH, and (2) a solid surface comprising an immobilized antibody having specific binding affinity towards a vitamin D moiety, and 3) a detecting reagent comprising an antibody having a binding affinity towards the complex formed between the immobilized antibody and the sample vitamin D moiety. The present kits can further comprise suitable washing reagents. The assay procedure may include wash steps between the different reagent additions.

In still another embodiments, the present kits comprise (1) a first assay reagent comprising a buffer of acidic pH; and (2) surface(s) or particles, e.g., magnetic particles, coated with an antibody having an affinity towards vitamin D moiety; and (3) an antibody labelled with a signaling molecule needed for chemiluminescence; and (4) a substrate (starter) or substrates needed for initiating the chemiluminescent reaction. The kit may also contain calibrators, controls, a dilution buffer and/or a washing buffer.

In yet another embodiments, the present invention provides a method for assaying a vitamin D moiety in a sample, which method comprises: a) contacting said sample with a first reagent comprising a buffer of acidic pH to dissociate said vitamin D moiety in said sample from its binding proteins; b) contacting said vitamin D moiety in said sample from step a) with a second reagent comprising particles, e.g., magnetic particles, coated with a first antibody that has a specific binding affinity to said vitamin D moiety to form a vitamin D moiety/first antibody complex; and c) contacting said vitamin D moiety/first antibody complex with a third reagent comprising a second antibody labelled with a signal generating moiety or molecule to form a complex among said vitamin D moiety, said first antibody and said second antibody labelled with a signal generating moiety or molecule; and d) assessing said signal from said complex among said vitamin D moiety, said first antibody complex and said second antibody to determine the presence, absence and/or amount of the vitamin D moiety in said sample. Optionally, the antibodies are different from a natural vitamin D binding protein for the vitamin D moiety. In some embodiments, the signal generating molecule is selected from the group consisting of acridinium ester, isoluminol, alkaline phosphatase, horse radish peroxidase and fluoresin.

The above kits can be used in a method for assaying a vitamin D moiety in a sample, which method comprises: a) forming a mixture of a sample and the first assay reagent and incubating the mixture for a period of time; and b) contacting the mixture with the surface(s) or particles, e.g., magnetic particles, coated with the first antibody specific for binding with vitamin D moiety, and c) after an incubation period of time, followed by a washing step, and d) resuspending the surface(s) or particles, e.g., magnetic particles, and contacting with the second antibody which is specific for the complex formed between the first antibody on surface(s) or particles, e.g., magnetic particles, and the sample vitamin D moiety and labelled with a signaling molecule for chemiluminescence; and e) after a period of incubation followed by another washing step, the surface(s) or magnetic particles are mixed with a starter or substrates that triggers the chemiluminescent reaction. The chemiluminescent intensity (RLU) is detected to determine the presence, absence and/or amount of the vitamin D moiety in the sample.

The present reaction mixtures or kits can be formulated or arranged in any suitable fashion or manner. In some embodiments, the present reaction mixtures or kits are contained in a single phase or homogenous phase. In other embodiments, the present reaction mixtures or kits are contained in multiple phases (heterogeneous assay), e.g., two or three phases.

Optionally, the antibodies in the above kits and methods are different from a natural vitamin D binding protein for the vitamin D moiety.

The present kits can be configured to be conducted within any suitable reaction time. In some embodiments, the present kits can be configured to have a total assay time that is at about 60 minutes or shorter, e.g., about 59, 58, 57, 56, 55, 54, 53, 52, 51, 50, 49, 48, 47, 46. 45., 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute. For example, the present kits can be configured to have an assay time from initiation, e.g., addition of a sample and/or a reagent(s), to signal readout time, that is at about 60 minutes or shorter, e.g., about 59, 58, 57, 56, 55, 54, 53, 52, 51, 50, 49, 48, 47, 46. 45., 44, 43, 42, 41, 40, 39, 38, 37, 36, 35, 34, 33, 3, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2 minutes or 1 minute.

The present kits can be configured to achieve any suitable precision. In some embodiments, the present kits can be configured to achieve a precision or CV of about 30% or less, e.g., about 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or less. For example, the present kits can be configured to achieve a precision or CV of about 5% or less, e.g., about 5%, 4%, 3%, 2.5%, 2%, 1.5% 1%, 0.5% or less for a vitamin D moiety level of about 30 ng/ml or less, e.g., about 30 ng/ml, 25 ng/ml, 20 ng/ml, 15 ng/ml, 10 ng/ml, 5 ng/ml, 4 ng/ml, 3 ng/ml, 2 ng/ml, 1 ng/ml, or less. In another example, the present kits can be configured to achieve a precision or CV of about 10% or less, e.g., about 10%, 9%, 8%, 7%, 6%, 5%, 4.5%, 4.0%, 3%, 2.5%, 2%, 1.5% 1%, 0.5% or less for a vitamin D moiety level of about 100 ng/ml or less, e.g., about 100 ng/ml, 90 ng/ml, 80 ng/ml, 70 ng/ml, 60 ng/ml, 50 ng/ml, 40 ng/ml, 30 ng/ml, 20 ng/ml, 10 ng/ml, or less.

D. Exemplary Embodiments

In some embodiments, the present invention provides a method, e.g., a homogeneous or a heterogeneous method, for determining total 25-hydroxy-vitamin D 25(OH)D concentrations in a sample, e.g., blood samples, wherein the dissociation of 25(OH)D from vitamin D binding proteins (VBP), the binding of the dissociated [25(OH)D] or free 25(OH)D with two monoclonal antibodies that forms antibody-vitamin D-antibody complex, and the detection of 25(OH)D in the sample is carried out in a single reaction mixture without phase separation or washing steps involved.

Of particular advantage of the embodiments is the significantly shorter total assay time (often <13 min in a homogenous assay format) and its user friendly homogenous assay format that eliminates the needs for sample pretreatment or phase separation/washing steps, and that allows the assay to be easily adapted for uses on general chemistry analyzers that are routinely used in clinical laboratories.

In some embodiments, the present invention provides a method of assaying a sample of blood or blood components for determining the amount of 25-hydroxy-vitamin D comprising: a) mixing the sample with a buffer of acidic pH that is capable of dissociating 25(OH)D from its binding protein; b) adding two monoclonal antibodies that are separately coated on latex particles, with one antibody or the first antibody having an affinity specifically towards the vitamin D moiety, and the other antibody or the second antibody having an affinity specifically towards the complex formed between the first antibody and the vitamin D moiety; and c) determining the concentration of 25(OH)D in the sample with a single reaction mixture, wherein the vitamin D binding proteins are not removed from the sample, and no phase separation or washing steps are involved.

In some embodiments, the acidic pH buffer is sodium acetate buffer containing appropriate amount of salts, polymers such as PEG 100k and detergents. The pH of the acidic buffer can be ranged from 2.5 to 6.5. The acidic pH buffer can also be sodium citrate buffer or phosphoric acid buffer or other buffer that has a buffer function in the acidic pH range.

In some embodiments, the latex particles have the diameter sizes from 30 nm to 500 nm, preferably from 120 nm to 360 nm.

In some embodiments, the sample is biological fluids including but not limited to whole blood, plasma, serum, and urine.

In some embodiments, the concentration of 25(OH)D includes the total concentration of 25(OH)D including 25(OH)D3 and 25(OH)D2.

In some embodiments, the assay format of the homogenous method of 25(OH)D determination is the particle-enhanced immunoturbidimetric methods. In other embodiments, the assay format of the homogenous method of 25(OH)D determination is the particle-enhanced immunonephelometric methods. In still other embodiments, the assay format of 25(OH)D determination is the heterogeneous magnetic particle (beads) based immunoassay methods.

In some embodiments, the assay format of the heterogeneous method of 25(OH)D determination is an enzyme-linked immunosorbent assay (ELISA) method.

Any suitable antibodies can be used. In some embodiments, the antibody is polyclonal. In other embodiments, the antibody is monoclonal.

Any suitable particles can be used. In some embodiments, the particles are nano-particle including but not limited to particles made of polystyrene, polymethyl methacrylate, polymethyl naphthalene, carbon 60, co-polymer of styrene, acrylic acid, naphathalene, magnetic particles, gold, silver, silica, silicon dioxide, chromium dioxide, and titanium dioxide.

In some embodiments, the present invention provides a kit for determining 25(OH)D in a sample, the kit comprises 2 reagents including (1) a buffer of acidic pH capable of dissociating 25(OH)D from its binding protein; and (2) latex particles separately coated with two monoclonal antibodies, with one antibody or the first antibody having binding affinity towards the vitamin D moiety, and the other antibody or the second antibody having a binding affinity towards the complex formed between the first antibody and the vitamin D moiety. In an exemplary assay, samples such as plasma or serum are mixed with the acidic pH buffer, and incubated for a short period of time before addition of the second reagent containing the antibodies conjugated on latex particles. The 25(OH)D concentration in the sample is quantified by measuring the optical change of the reaction mixture and using a set of 25(OH)D calibrators.

In some embodiments, the present invention provides a kit for determining 25(OH)D in a sample, the kit comprises 2 reagents including (1) a buffer of acidic pH capable of dissociating 25(OH)D from its binding protein (partially or entirely); and (2) a reagent containing two antibodies that are separately conjugated on particles with one antibody having a binding affinity towards vitamin D moiety, and the other antibody having binding affinity towards the complex formed between the first antibody and the vitamin D moiety. In an exemplary assay, samples such as plasma or serum are mixed with the acidic pH buffer, and incubated for a short period of time before addition of the second reagent containing the antibodies coated on particles. The 25(OH)D concentration in the sample is quantified by measuring the optical change of the reaction mixture and using a set of 25(OH)D calibrators.

In some embodiments, the present invention provides a kit for determining 25(OH)D in a sample, the kit contains a dissociation solution comprising an acidic pH buffer. This kit can be used in the ELISA format with microtiter plates for 25(OH)D determination.

In some embodiments, the exemplary vitamin D assays use magnetic particles coupled with chemiluminescent or fluorescent signaling molecules. The vitamin D assay method uses magnetic particles coated with one monoclonal or polyclonal antibody having a binding affinity towards the vitamin D moiety, and uses another antibody labeled with chemiluminescent detection molecules and having a binding affinity towards the complex formed between the antibody coated on the magnetic particles and vitamin D moiety. After incubations and washing steps, the vitamin D concentrations in the samples are determined based on the signal intensity (RLU) of chemiluminescence and a calibration curve.

In some embodiments, the exemplary vitamin D assays have certain advantages over the vitamin D assays in the art. Exemplary advantages include one or more of the following: fast or fastest Vitamin D assay (results in ~10 minutes or less); universal Vitamin D assay for general chemistry analyzers; liquid stable, ready-to-use two reagents system; liquid stable calibrators and controls; automation or full automation; no requirement for pretreatments or pre-dilutions steps; equal recognition of 25-OH Vitamin D2 and 25-OH Vitamin D3; amenable to high throughput on clinical chemistry analyzers; and/or traceable to NIST SRM972. Further exemplary advantages include one or more of the following: fast testing time (less than 10 minutes); two reagent format which is a user friendly assay for vitamin D; and/or assay format adaptable to many or all automated clinical chemistry analyzers which are the most commonly used instruments in all sizes of clinical laboratories. In some embodiments, these advantages make it possible for using the exemplary vitamin D assay as a true routine clinical test.

The present invention is further illustrated by the following exemplary embodiments.

1. A method for assaying a vitamin D moiety in a sample, which method comprises: a) contacting a sample containing or suspected of containing a vitamin D moiety with a buffer that is capable of dissociating a vitamin D moiety from its binding protein and/or a buffer of acidic pH, and two or more antibodies with at least one antibody or the first antibody having a binding affinity specifically towards vitamin D moiety, and another antibody (second antibody) having binding affinity towards the complex formed between the first antibody and the vitamin D moiety; and b) assessing binding between said specific antibodies and said vitamin D moiety to determine the presence, absence and/or amount of said vitamin D moiety in said sample. The buffer of acidic pH can comprise any suitable salt, polymer and/or detergent.

2. The method of embodiment 1, which does not comprise a step of removing the natural vitamin D binding protein for the vitamin D moiety prior to assessing binding between the specific antibodies and the vitamin D moiety.

3. The method of embodiment 1 or 2, which does not comprise a wash step.

4. The method of any of embodiments 1-3, which is conducted as a homogeneous assay.

5. The method of any of embodiments 1-4, wherein the sample is contacted with a single reaction mixture comprising a buffer of acidic pH and latex particles coated with two antibodies separately, with one antibody or the first antibody having a binding affinity towards the vitamin D moiety and the other antibody or the second antibody having a binding affinity towards the complex formed between the first antibody and the vitamin D moiety.

6. The method of any of embodiments 1-5, which does not comprise a step of contacting the sample with 8-anilino-1-napthalenesulfonic acid ammonium salt and/or 3-(acetonyl-benzyl)-4-hydroxycoumarin.

7. The method of any of embodiments 1-5, which does not comprise a step of contacting the sample with a non-competitive displacement agent that separates the vitamin D moiety from its binding protein in the sample.

8. The method of any of embodiments 1-7, wherein the pH in a final reaction mixture (acidic pH buffer plus sample plus latex particles) is at 3.0 or higher.

9. The method of any of embodiments 1-8, wherein the pH in a final reaction mixture comprising the sample, the acidic pH buffer and the latex particles is at 13 or lower.

10. The method of any of embodiments 1-9, which does not comprise a step of contacting the sample with a vitamin D releasing composition comprising a cyclodextrin, a sodium salicylate and NaOH.

11. The method of any of embodiments 1-10, which does not comprise a step of contacting the sample with a perfluoro alkyl acid, or a salt thereof, to release 25(OH)D from vitamin D binding protein.

12. The method of any of embodiments 1-11, which does not comprise a step of contacting the sample with a serine protease with endo- and exoproteolytic activity to digest vitamin D binding proteins in the sample.

13. The method of any of embodiments 1-12, which is used to assess status of the vitamin D moiety in a subject, and the sample is a biological sample obtained and/or derived from the subject.

14. The method of embodiment 13, wherein the subject is a mammal.

15. The method of embodiment 14, wherein the mammal is a human.

16. The method of any of embodiments 13-15, wherein the sample is a biological fluid.

17. The method of embodiment 16, wherein the biological fluid is selected from the group consisting of whole blood, plasma, serum and urine.

18. The method of any of embodiments 1-17, wherein the vitamin D moiety is 25-hydroxy-vitamin $D_3$, 25-hydroxy-vitamin $D_2$, a vitamin D metabolite or 1,25-dihydroxy-vitamin $D_3$ (1,25-$(OH)_2D_3$).

19. The method of embodiment 18, wherein the vitamin D metabolite is 25-hydroxy-vitamin D (25(OH)D).

20. The method of embodiment 19, wherein the 25(OH)D is 25(OH)D3.

21. The method of embodiment 19, wherein the 25(OH)D is 25(OH)D2.

22. The method of embodiment 19, wherein the 25(OH)D is a sum of 25(OH)D2 and 25(OH)D3.

23. The method of any of embodiments 1-22, wherein the acidic pH buffer is sodium acetate buffer containing suitable amount of salts such NaCl, polymers such as PEG 100k and detergent such as Tween 20. The acidic pH buffer can also be sodium citrate buffer, or phosphoric acid buffer, or a combination thereof.

24. The method of embodiment 23, wherein the pH of the acidic buffer is ranging from 2.5 to 6.5, preferably from 4.0 to 5.5.

25. The method of any of embodiments 1-24, wherein the monoclonal antibodies are those with at least one antibody or the first antibody having a specific binding affinity against the vitamin D moiety and with another antibody or the second antibody having a specific binding affinity against the complex formed between the first antibody and the vitamin D moiety.

26. The method of embodiment 25, wherein one antibody or the first antibody specifically binds to 25(OH)D3 or 25(OH)D2.

27. The method of embodiment 25, wherein one antibody or the second antibody specifically binds to the complex formed between the first antibody and the vitamin D moiety.

28. The method of embodiments 25-27, wherein the antibodies are monoclonal antibodies.

29. The method of embodiment 25-27, wherein the antibodies are polyclonal antibodies or combination of monoclonal antibody and polyclonal antibodies.

30. The method of any of embodiments 1-29, which is conducted using a particle-enhanced immunoturbidimetric method.

31. The method of any of embodiments 1-29, which is conducted using a particle-enhanced immunonephelometric method.

32. The method of any of embodiments 1-29, which is conducted using a magnetic particle (beads) based immunoassay method.

33. The method of any of embodiments 30-33, wherein the particle comprises polystyrene, polymethyl methacrylate, polymethyl naphthalene, poly(divinylbenzene), polyvinyl naphthalene, co-polymer of styrene, acrylic acid divinylbenzene, naphathalene, carbon 60, magnetic beads, gold, silver, silica, silicon dioxide, chromium dioxide, and/or titanium dioxide.

34. The method of any of embodiments 30-33, wherein the particle is a nanoparticle.

35. The method of embodiment 34, wherein the nanoparticle has a diameter ranging from about 30 nm to about 500 nm.

36. The method of any of embodiments 1-35, which is conducted using a homogeneous or a heterogeneous assay format.

37. The method of any of embodiments 1-36, which is conducted using a sandwich or competitive assay format.

38. The method of any of embodiments 1-37, which is a homogenous assay conducted in a single reaction mixture without phase separation or washing step.

39. The method of any of embodiments 1-38, the total assay time for homogeneous format is less than 30 min, typically less than 15 min, and the total assay time for heterogeneous assay format is less than 60 min, typically less than 45 min.

40. The method of any of embodiments 1-39, which is conducted on a general chemistry analyzer or a clinical chemistry analyzer.

41. The method of embodiment 40, wherein the general chemistry analyzer or clinical chemistry analyzer includes but not limited to Roche, Hitachi, Modular P, Cobas series, Beckman/Olympus AU series, Beckman Synchron and DXC series, or Abbot Architect series.

42. A kit for assaying a vitamin D moiety in a sample, which kit comprises: a) a buffer that is capable of dissociating a vitamin D moiety from its binding protein and/or a buffer of acidic pH; and b) particles, e.g., latex particles, coated, e.g., separately coated, with at least two antibodies of which one, or the first one, has a specific binding affinity towards the vitamin D moiety, and another antibody, or the second antibody, has a specific binding affinity towards the complex formed between the first antibody and the vitamin d moiety.

43. The kit of embodiment 42, which further comprises means for assessing binding between vitamin D moiety and the antibodies coated on latex particles to determine the presence, absence and/or amount of the vitamin D moiety in the sample.

44. The kit of embodiment 43, which comprises reagents: (1) a first assay reagent comprising a buffer of acidic pH containing salts, polymer and detergent; (2) a second assay reagent comprising a suspension of latex particles coated with at least two antibodies with one antibody or the first antibody having a binding affinity towards the vitamin D moiety, and the other antibody or the second antibody or antibodies having a specific binding affinity towards the complex formed between the first antibody and the vitamin D moiety.

45. The kit of embodiment 44, which comprises: (1) a first assay reagent comprising a buffer of acidic pH; and (2) microtiter plate wells containing an immobilized antibody that specifically binds to a vitamin D moiety or its analog.

46. A method for assaying a vitamin D moiety in a sample using the kit of embodiment 44, which method comprises: a) forming a mixture of a sample, the first assay reagent for a period of time before adding the second assay reagent to the mixture; and b) quantifying the amount of 25(OH)D in the sample by measuring the optical change of the reaction mixture and using a set of 25(OH)D calibrators.

47. A method for assaying a vitamin D moiety in a sample using the kit of embodiment 45, which method comprises: a) forming a mixture of a sample and the first assay reagent in the microtiter plate wells, and incubating the mixture for a period of time; and b) contacting the mixture with the second antibody labelled with peroxidase (HRP) and incubating for a period of time; c) after a washing step, HRP substrate is added to the microtiter plate well and the color is developed for quantifying the presence, absence and/or amount of the vitamin D moiety in the sample.

48. A method for assaying a vitamin D moiety in a sample using the kit comprises of reagents including a buffer of acidic pH; magnetic particles coated with an antibody or the first antibody that specifically binds vitamin D moiety, and the second antibody that is labelled with signaling molecules and having a specific binding affinity towards the complex formed between the first antibody coated on the magnetic particles and the vitamin D moiety, wherein the signaling molecules are acridinium ester, isoluminol, alkaline phosphatase, horse radish peroxidase, fluroresin or any other chemiluminesence or fluorescence based signal molecules commonly used for signal detections.

49. A method for assaying a vitamin D moiety in a sample using the kit of embodiment 48, which method comprises: a) forming a mixture of a sample, the acidic pH buffer and magnetic particles coated with the first antibody, and incubating for a period of time; b) washing the magnetic particles and adding the second antibody labelled with signaling molecules and having a specifically binding affinity to the complex formed between the first antibody coated on the magnetic particles and the sample vitamin D moiety followed by a period of incubation time; c) washing the magnetic particles and adding the substrates (starters) if needed for the signal detection by the method of chemiluminescent or fluorescent detection.

50. A method for assaying a vitamin D moiety in a sample using the kit of embodiment 49, which method comprises: a) forming a mixture of a sample, the acidic pH buffer, the first antibody coated on magnetic particles and the second antibody labeled with signaling molecules and has a specific binding affinity towards the complex formed between the first antibody coated on the magnetic particles and the sample vitamin D moiety, and incubating for a period of time; b) washing the magnetic particles and addition of the substrates if needed for the signal detection by the method of chemiluminescent or fluorescent method.

51. The method of any of embodiments 1-41, wherein the another antibody (second antibody) specifically binds to an epitope on the vitamin D moiety that is not bound by one of the antibodies (or the first antibody).

52. The method of any of embodiments 1-41, wherein the another antibody (second antibody) binds or specifically binds to the one of the antibodies (or the first antibody).

EXAMPLES

Example 1: 25(OH)D Assay Kit

The latex particle enhanced immunoassay reagents used in this example are listed below:
Reagent 1
0.05M Sodium Acetate, pH 4.0
10% NaCl
5% Choline Chloride 0.5M MES
0.5% sugar
0.04% TWEEN 20
0.9% PEG 100k
0.09% NaN3
Reagent 2
0.6 M Tris, pH 8.0
0.1% BSA
10% Sucrose
0.2% TWEEN 20
0.05% first antibody-latex particle conjugate
0.08% second antibody-latex particle conjugate
0.09% NaN3

1. Assay Procedure with Beckman AU 680 Analyzer

Three (3) µL of sample was mixed with 16 µL of Reagent 1 inside a cuvette and incubated at 37° C. for about 3.5 min. Forty (40) µL of Reagent 2 was added to the mixture and incubated for about 4 min. The change in absorbance at 700 nm was measured using the assay parameters as indicated in the parameter sheet (Table 1) below. The assay procedure is also illustrated in FIG. 13.

TABLE 1

| Assay Parameters on AU 680 analyzer | |
|---|---|
| General | |
| Test Name: VITD  Type: Serum | Operation: Yes |
| Sample Volume 3.0 μl  Dilution 0 μl | Pre-Dilution Rate 1 |
| Reagents: | Min OD  Max OD |
| R1 volume 160 μl Dilution 0 μl | L:  H: |
| R2 volume 40 μl Dilution 0 μl | |
| Wavelength: | Reagent OD Limit: |
| Method: FIXED | First L: −2.000; First H: 3.000 |
| Reaction Slope: + | Last L: −2.000; Last H: 3.000 |
| Measuring Point 1: First 11; Last 22 | Dynamic Range: |
| Measuring Point 2: First; Last | L: H: |
| Linearity: | Correlation Factor: |
| No-Lag-Time: No | A: 1.0000 B: 0.000 |
| | Onboard stability Period |

| Calibration Type: 5AB Formula: Spline Counts: 2 Process: CONC | | | |
|---|---|---|---|
| Cal No. | CONC | Factor/OD-L | Factor OD-HOD |
| Point 1:1 | 0.00 | −2.00000 | 3.0000 |
| Point 2:2 | *.** | −2.00000 | 3.0000 |
| Point 3:3 | *.** | −2.00000 | 3.0000 |
| Point 4:4 | *.** | −2.00000 | 3.0000 |
| Point 5:5 | *.** | −2.00000 | 3.0000 |
| Point 6:6 | | | |
| Point 7: | | | |
| 1-Point Cal. Point | _with CONC-0 | Advanced Calibration: No | |
| MB type Factor: | | Calibration Stability Period: | |

1. Assay Calibration Curve (Example Only)

The 25(OH)D Assay kit was calibrated with serum based calibrators of known 25(OH)D concentrations. The calibration curve is shown in FIG. 1.

After successful calibration of the 25(OH)D assay kit, controls and linearity standards were tested. In addition, patient serum samples were tested and the results were compared with a FDA approved, commercially available vitamin D assay method (DiaSorin immunoassay method) as well as with a liquid chromatography-mass spectrophotometric (LC-MS) method for total vitamin D (considered as the gold standard for vitamin D test). The results are shown in Tables 1-3 below and FIGS. 2-6.

2. Results:

Assay precisions are illustrated in Table 2 below.

TABLE 2

| Vitamin D assay precisions Precision | | | | | | | |
|---|---|---|---|---|---|---|---|
| | Level 1 | Level 2 | Level 3 | Level 4 | Level 5 | Level 6 | Level 7 |
| Rep. 1 | 5.0 | 12.1 | 24.5 | 46.1 | 59.3 | 101.2 | 157.1 |
| Rep. 2 | 6.6 | 12.5 | 25.3 | 46.5 | 59.9 | 100.2 | 158.9 |
| Rep. 3 | 5.9 | 12.5 | 24.5 | 46.0 | 60.7 | 102.1 | 154.8 |
| Rep. 4 | 5.7 | 12.5 | 23.9 | 46.8 | 59.3 | 100.6 | 158.2 |
| Rep. 5 | 3.5 | 11.8 | 24.3 | 46.8 | 60.4 | 103.4 | 155.7 |
| Rep. 6 | 4.7 | 12.0 | 24.8 | 46.9 | 60.0 | 99.2 | 157.3 |
| Rep. 7 | 5.7 | 12.0 | 24.4 | 46.1 | 60.0 | 102.0 | 163.4 |
| Rep. 8 | 5.2 | 12.5 | 24.8 | 46.4 | 59.7 | 101.5 | 158.4 |
| Rep. 9 | 4.2 | 12.5 | 24.7 | 47.1 | 59.9 | 102.6 | 161.6 |
| Rep. 10 | 4.9 | 12.1 | 24.6 | 46.9 | 60.2 | 100.8 | 159.1 |
| Rep. 11 | 3.5 | 12.5 | 24.6 | 47.1 | 60.5 | 103.3 | 161.1 |
| Rep. 12 | 2.9 | 12.3 | 24.9 | 46.4 | 60.4 | 101.7 | 155.7 |
| Mean (ng/ml) | 4.8 | 12.3 | 24.6 | 46.6 | 60.0 | 101.6 | 158.4 |
| % CV | 23.1% | 2.1% | 1.4% | 0.8% | 0.7% | 1.2% | 1.6% |

Assay linearity on AU 680 analyzer is illustrated in FIG. 2. Assay accuracy in comparison with DiaSorin Liason method is illustrated in FIG. 3. Assay accuracy in comparison with LC-MS/MS method is illustrated in FIG. 4.

Example 2: 25(OH)D Assay Kit

Magnetic particle based chemiluminescent immunoassay reagents used are listed in this example:
Reagent 1:
0.05M Sodium Acetate buffer, pH 4.0
8% NaCl
1.2% Sucrose
0.05% TWEEN 20
0.09% NaN3
Reagent 2:
1×PBS buffer, pH 7.4
0.3% BSA
0.04% TWEEN 20
0.09% NaN3
0.1 mg/ml magnetic particles coated with the first antibody
Reagent 3:
1×PBS buffer, pH 8.0
0.2% BSA
0.04% TWEEN 20
1 ug/ml ABEI-labelled second antibody
NaN3 0.09%
Starter (Substrates):
a) 5% NaOH; b) 0.1% Peroxide
Washing Solution:
0.1 M Tris-HCl buffer and detergent.
Assay Procedure Using a Commercially Available Instrument:

Five ul (5 ul) of serum Sample was mixed with 180 ul of the Reagent 1, and incubate for 5 min to dissociate the vitamin D in the sample from its binding proteins. Aspirate 100 ul of the above sample/reagent 1 mixture, and mix with 20 ul of the Reagent 2, and incubate for 20 min before addition of 50 ul of Reagent 3. After another 10 min of incubation, the magnetic particles were washed by the washing buffer for 3 times. 200 ul of Substrates were added and the chemiluminescent intensity or RLU was read for 3 seconds. The vitamin D content in the sample was determined based on the RLU and the calibration curve established under the same assay conditions.

Results:

An exemplary calibration curve of chemiluminesent detection method is illustrated in FIG. 5. Assay precisions (10 repeats for each level of controls) are illustrated in Table 3 below. Comparative data between an exemplary method of the present disclosure and a commercially available predicate method (immunoassay) on assay accuracy is illustrated in FIG. 6.

TABLE 3

Assay precisions (10 repeats for each level of controls)

|  | Vit. D Control I | Vit. D Control II | Vit. D Control III |
|---|---|---|---|
| Conc. ng/ml | 10.5 | 30.1 | 60.9 |
| CV % | 3.4% | 2.9% | 2.2% |

Example 3: Analytical Performance a. Precision/Reproducibility

Precision of an exemplary Diazyme vitamin D assay (latex particle enhanced immunoassay in Example 1) was evaluated according to the Clinical and Laboratory Standards Institute (CLSI) EP5-A2 guideline. Precision assessment was performed on the Beckman AU680 chemistry analyzer. In the study, three lots of reagents were used. For each reagent lot, 12 specimens were tested: 2 vitamin D controls and 10 vitamin D human serum samples. The tested serum samples coming with IRB-approval were obtained from a commercial source (PromedDx) and covered the dynamic range of the assay. As recommended by the CLSI EP5-A2 protocol, precision samples were tested in duplicates per run and two runs per day over 20 working days. Eighty (80) data points were obtained per specimen and per reagent lot.

The precision results obtained for one representative lot of reagents is summarized Table 4 below.

TABLE 4

| Sample | Mean (N = 80) | Within-Run SD | Within-Run % CV | Total SD | Total % CV |
|---|---|---|---|---|---|
| Control 1 | 22.3 | 0.92 | 4.2% | 1.33 | 6.0% |
| Control 2 | 43.7 | 1.07 | 2.4% | 1.40 | 3.2% |
| Sample 1 | 11.1 | 0.87 | 7.8% | 1.86 | 16.7% |
| Sample 2 | 14.1 | 0.75 | 5.3% | 2.14 | 15.1% |
| Sample 3 | 18.6 | 0.86 | 4.6% | 1.69 | 9.0% |
| Sample 4 | 22.1 | 0.86 | 3.9% | 1.41 | 6.4% |
| Sample 5 | 43.4 | 0.89 | 2.1% | 1.22 | 2.8% |
| Sample 6 | 59.7 | 1.17 | 2.0% | 1.89 | 3.2% |
| Sample 7 | 80.6 | 1.32 | 1.6% | 2.31 | 2.9% |
| Sample 8 | 99.8 | 2.32 | 2.3% | 3.25 | 3.3% |
| Sample 9 | 118.5 | 2.27 | 1.9% | 4.11 | 3.5% |
| Sample 10 | 140.0 | 3.58 | 2.6% | 4.34 | 3.1 | b. Linearity/Assay Reportable Range

Linearity of the exemplary Diazyme vitamin D assay was evaluated using the CLSI EP6-A guideline (Evaluation of the Linearity of Quantitative Analytical Methods; approved: 2003).

Acceptance Criteria

Linear regression of measured values versus expected values has a slope of 1.0±0.05 and a correlation coefficient $R^2 > 0.95$.

The linearity study was performed on the Beckman AU680 chemistry analyser. A human serum sample was spiked with a vitamin D stock solution to a concentration of 156.3 ng/mL (as measured in triplicates using the exemplary Diazyme vitamin D assay). Vitamin D stock material was purchased from Sigma-Aldrich and molar concentrations were calculated using the information provided by the certificate of analysis. Thus prepared high sample was diluted with a low sample measuring 4.3 ng/mL (as measured in triplicates using the exemplary Diazyme vitamin D assay) to create a total of 11 linearity levels as follows:

Level 01: 1.00 ml Low Sample+0.00 ml of High Sample
Level 02: 0.90 ml Low Sample+0.10 ml of High Sample
Level 03: 0.80 ml Low Sample+0.20 ml of High Sample
Level 04: 0.70 ml Low Sample+0.30 ml of High Sample
Level 05: 0.60 ml Low Sample+0.40 ml of High Sample
Level 06: 0.50 ml Low Sample+0.50 ml of High Sample
Level 07: 0.40 ml Low Sample+0.60 ml of High Sample
Level 08: 0.30 ml Low Sample+0.70 ml of High Sample
Level 09: 0.20 ml Low Sample+0.80 ml of High Sample
Level 10: 0.10 ml Low Sample+0.90 ml of High Sample
Level 11: 0.00 ml Low Sample+1.00 ml of High Sample The linearity set prepared above was tested with the exemplary Diazyme vitamin D assay in triplicate using one lot of reagents. The linearity test results are shown in the Table 5 below and in FIG. 7.

TABLE 5

| Level | Rep. 1 | Rep. 2 | Rep. 3 | Measured (ng/mL) | Expected (ng/mL) | % Deviation |
|---|---|---|---|---|---|---|
| Level 1 | 3.5 | 4.4 | 5.0 | 4.3 | 4.3 | 0.0% |
| Level 2 | 22.4 | 21.3 | 20.4 | 21.4 | 19.5 | 9.6% |
| Level 3 | 38.0 | 35.6 | 37.6 | 37.1 | 34.7 | 6.8% |
| Level 4 | 49.7 | 53.7 | 51.0 | 51.5 | 49.9 | 3.1% |
| Level 5 | 66.4 | 66.1 | 65.4 | 66.0 | 65.1 | 1.3% |
| Level 6 | 83.6 | 78.9 | 81.4 | 81.3 | 80.3 | 1.2% |
| Level 7 | 94.0 | 94.1 | 91.9 | 93.3 | 95.5 | -2.3% |
| Level 8 | 113.0 | 110.7 | 110.0 | 111.2 | 110.7 | 0.5% |
| Level 9 | 126.9 | 122.9 | 121.1 | 123.5 | 125.9 | -2.0% |
| Level 10 | 143.7 | 138.0 | 138.9 | 140.2 | 141.1 | -0.7% |
| Level 11 | 157.3 | 157.1 | 154.6 | 156.3 | 156.3 | 0.0% |

Example 4: Comparison Studies a. Method Comparison with Predicate Device

For this method comparison study, individual serum samples were tested with the exemplary Diazyme vitamin D assay (latex particle enhanced immunoassay in Example 1) and compared to the predicate device (DiaSorin Liaison LX). The serum samples were obtained from a commercial source, Biochemed and came with IRB-approval. Samples that returned values outside the dynamic range of the assay were excluded. A total of 40 unaltered samples spanning assay AMR were used in the assessment of accuracy. Results are shown FIG. 8.

b. Matrix Comparison

To evaluate the effect of anticoagulants, the exemplary Diazyme vitamin D assay was used to measure the 25-OH Vitamin D concentrations of matched sets of serum, $K_2$-EDTA, $K_3$-EDTA plasma and Li-Heparin plasma. The samples used in this study were obtained from a certified commercial source (ProMedDx, LLC). All tested samples were collected according to an IRB approved protocol by the commercial vendor. The reported values for each sample and for each matrix were obtained from single measurements. The total number of matched sets tested was 54. In order to cover the claimed measuring range for each matrix, seven spiked patient samples were included in the study. Results are shown FIGS. 9-11.

Example 5: Exemplary Diazyme Vitamin D Chemiluminescence Assay

An exemplary Diazyme vitamin D chemiluminescence assay is composed of 3 reagents: magnetic beads conjugated with the first antibody; extraction buffer; and the second antibody conjugated with ABEI molecule (ISO-lumina) as described in Example 2. The assay procedure is shown in Table 6 below:

TABLE 6

| Assay procedure Diazyme Chemiluminescence Assay Format | |
|---|---|
| Sample/acidic buffer/Beads | 2 ul + 50 ul + 20 ul |
| Incubation | 15 min |
| ABEI/AE Label | 150 ul |
| Incubation | 15 min |
| Cycle washing (3 cycles) | 400 ul |
| Measurement | 3 seconds |

The exemplary Diazyme vitamin D chemiluminescence Assay was compared to Roche VD assay. The comparison results are shown in FIG. 12. Precision of the exemplary Diazyme vitamin D chemiluminescence Assay is shown in Tables 7 and 8 below.

TABLE 7

| Assay precisions | |
|---|---|
| Sample | Vitamin D (ng/ml) |
| 1 | 17.5 |
| 2 | 16.3 |
| 3 | 17.4 |
| 4 | 17.6 |
| 5 | 16.8 |
| 6 | 16.9 |
| 7 | 16.9 |
| 8 | 17.3 |
| 9 | 16.5 |
| 10 | 16.5 |
| 11 | 16.9 |
| 12 | 17.4 |
| 13 | 16.4 |
| 14 | 16.1 |
| 15 | 16.6 |
| 16 | 16.3 |
| 17 | 16.9 |
| 18 | 17.1 |
| 19 | 17.2 |
| 20 | 17.2 |
| Mean | 16.9 |
| Stdev | 0.4 |
| CV | 2.6% |

TABLE 8

| Assay precisions | |
|---|---|
| Sample | Vitamin D (ng/ml) |
| 21 | 70 |
| 22 | 64.2 |

TABLE 8-continued

| Assay precisions | |
|---|---|
| Sample | Vitamin D (ng/ml) |
| 23 | 68.6 |
| 24 | 64.5 |
| 25 | 60.0 |
| 26 | 69.8 |
| 27 | 63.1 |
| 28 | 66.7 |
| 29 | 67.2 |
| 30 | 65.1 |
| 31 | 67.4 |
| 32 | 65.5 |
| 33 | 64.7 |
| 34 | 67.4 |
| 35 | 69.6 |
| 36 | 60.9 |
| 37 | 64.5 |
| 38 | 66.4 |
| 39 | 60.4 |
| 40 | 63.9 |
| Mean | 65.5 |
| Stdev | 3.0 |
| CV | 4.5% |

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The invention claimed is:

1. A method for assaying 25-hydroxyvitamin D (25(OH) D) in a sample, which method comprises:
    a) contacting a sample containing or suspected of containing 25(OH)D with a buffer of acidic pH in the range from 2.5 to 6.9, and at least two monoclonal antibodies that are separately conjugated to nanoparticles, wherein at least one of said antibodies (or the first antibody) has a specific binding affinity towards said 25(OH)D, and at least another said antibody (or the second antibody) has a specific binding affinity towards the complex formed between the first antibody and said 25(OH)D; and
    b) assessing binding between said monoclonal antibodies and said 25(OH)D to determine the presence, absence and/or amount of said 25(OH)D in said sample,
    wherein said method is conducted as a homogeneous assay using a particle-enhanced immunoturbidimetric method, said method does not comprise a wash step and is completed within 30 minutes or less, and said method is conducted to achieve a precision or CV of 10% or less for 25(OH)D level from 30 ng/ml to 100 ng/ml.

2. The method of claim 1, wherein the sample is contacted with a single reaction mixture comprising the buffer of acidic pH, and paired antibodies separately conjugated to nanoparticles, with one antibody or the first antibody having a specific binding affinity towards the 25(OH)D and the other antibody or the second antibody having a specific binding affinity towards the complex formed between the first antibody and the 25(OH)D.

3. The method of claim 1, wherein the pH in a final reaction mixture comprising the sample, the acidic pH buffer and monoclonal antibodies conjugated to nanoparticles ranges from 3.0 to 13.

4. The method of claim 1, which is used to assess status of the 25(OH)D in a subject, and the sample is a biological sample obtained and/or derived from the subject.

5. The method of claim 1, wherein the 25(OH)D is 25(OH)$D_2$, 25(OH)$D_3$ or a sum of 25(OH)$D_2$ and 25(OH)$D_3$.

6. The method of claim 1, wherein the acidic pH buffer is the sodium acetate buffer, or sodium citrate buffer, or phosphoric acid buffer, a combination thereof, or any buffer having a buffer function in the acidic pH range.

7. The method of claim 1, wherein the first antibody and the second antibody are separately conjugated to nanoparticles, and used either as a single combined reagent or used as two separated reagents in the assay procedure.

8. The method of claim 1, wherein the acidic pH buffer contains a salt, polymer, and/or a detergent that allows for partial or total dissociation of 25(OH)D from its binding protein(s) within a period of time less than 30 minutes.

9. The method of claim 8, wherein the salt, polymer, and/or a detergent is included in the acidic pH buffer, or in a separated reagent solution used to mix with the acidic pH buffer in the assay procedure.

10. The method of claim 1, wherein the nanoparticles comprise a material selected from the group consisting of polystyrene, polymethyl methacrylate, polymethyl naphthalene, poly(divinylbenzene), polyvinyl naphthalene, co-polymer of styrene, acrylic acid divinylbenzene, naphthalene, carbon 60, magnetic beads, gold, silver, silica, silicon dioxide, chromium dioxide, and titanium dioxide.

11. The method of claim 1, wherein latex particles are used, and the particle sizes (diameters) range from 30 nm to 500 nm.

12. The method of claim 1, wherein the assay is completed within 20 minutes or less.

13. The method of claim 1, wherein the assay is conducted with a general chemistry analyzer or a clinical chemistry analyzer.

14. A method for assaying 25-hydroxyvitamin D (25(OH)D) in a sample, which method comprises: a) forming a mixture of a sample and a first assay reagent and incubating the mixture for a period of time before adding a second assay reagent to the mixture; and b) quantifying the amount of 25(OH)D in the sample by measuring the optical change of the reaction mixture and using a set of 25(OH)D calibrators,
wherein the first assay reagent comprises a buffer of acidic pH in the range from 2.5 to 6.9 and containing a salt, a polymer and/or a detergent, and the second assay reagent comprises a paired monoclonal antibodies separately conjugated to nanoparticles, with one antibody or the first antibody having a specific binding affinity to 25(OH)D, and with another antibody or the second antibody having a specific binding affinity to the complex formed between the first antibody and the 25(OH)D, and
said methid is conducted using a particle-enhanced immunoturbidimetric method to achieve a precision or CV of 10% or less for 25(OH)D level from 30 ng/ml to 100 ng/ml, said method does not comprise a wash step and is completed within 30 minutes or less.

* * * * *